(12) United States Patent
Song et al.

(10) Patent No.: US 12,229,141 B2
(45) Date of Patent: Feb. 18, 2025

(54) LINKING INDIVIDUAL DATASETS TO A DATABASE

(71) Applicant: Ancestry.com DNA, LLC, Lehi, UT (US)

(72) Inventors: Shiya Song, San Mateo, CA (US);
Jingwen Pei, San Mateo, CA (US);
Brett Frederick Jorgensen, Draper, UT (US); Aaron James Stern, Berkeley, CA (US); Ross E. Curtis, Cedar Hills, UT (US)

(73) Assignee: Ancestry.com DNA, LLC, Lehi, UT (US)

( * ) Notice: Subject to any disclaimer, the term of this patent is extended or adjusted under 35 U.S.C. 154(b) by 23 days.

(21) Appl. No.: 17/868,775

(22) Filed: Jul. 20, 2022

(65) Prior Publication Data

US 2022/0365934 A1 Nov. 17, 2022

Related U.S. Application Data

(63) Continuation of application No. 17/128,009, filed on Dec. 19, 2020, now Pat. No. 11,429,615.
(Continued)

(51) Int. Cl.
*G06F 15/16* (2006.01)
*G06F 16/22* (2019.01)
(Continued)

(52) U.S. Cl.
CPC .... *G06F 16/24558* (2019.01); *G06F 16/2246* (2019.01); *G06F 16/24578* (2019.01); *G16B 10/00* (2019.02)

(58) Field of Classification Search
None
See application file for complete search history.

(56) References Cited

U.S. PATENT DOCUMENTS 6,570,567 B1 5/2003 Eaton
7,062,752 B2 6/2006 Simpson et al.
(Continued)

FOREIGN PATENT DOCUMENTS

WO WO 02/17190 A1 2/2002
WO WO 2016/061568 A1 4/2016

OTHER PUBLICATIONS

Alexander, D.H., et al., "Fast model-based estimation of ancestry in unrelated individuals," Genome research, Sep. 2009, vol. 19, No. 9, pp. 1655-1664.
(Continued)

*Primary Examiner* — Alex Gofman
(74) *Attorney, Agent, or Firm* — Fenwick & West LLP

(57) ABSTRACT

The disclosed system links an individual dataset to a database. The system receives a target individual dataset associated with a target individual and identifies candidate individual datasets that are potentially related to the target individual dataset. The system identifies a related individual dataset that has data bits that match some data bits in the target individual dataset. The system then identifies a parent node that is a common parent node to both the target individual dataset and the related individual dataset. The system retrieves a data tree that the parent node belongs to with the data tree containing information describing inter-relationships among datasets in the data tree. A node in the data tree is identified to assign the target individual dataset based on strings of matched data bits and number of the matched strings between the target individual dataset and the datasets in the data tree.

18 Claims, 22 Drawing Sheets

Related U.S. Application Data

(60) Provisional application No. 62/951,646, filed on Dec. 20, 2019.

(51) Int. Cl.
*G06F 16/2455* (2019.01)
*G06F 16/2457* (2019.01)
*G16B 10/00* (2019.01)

(56) References Cited

U.S. PATENT DOCUMENTS

| | | | |
|---|---|---|---|
| 7,249,129 | B2 | 7/2007 | Cookson et al. |
| 7,818,281 | B2 | 10/2010 | Kennedy et al. |
| 8,510,057 | B1 | 8/2013 | Avey et al. |
| 8,769,438 | B2 | 7/2014 | Mangum et al. |
| 9,116,882 | B1 | 8/2015 | Macpherson et al. |
| 9,213,947 | B1 | 12/2015 | Do et al. |
| 9,239,835 | B1 | 1/2016 | Tiwari et al. |
| 9,336,177 | B2 | 5/2016 | Hawthorne et al. |
| 9,367,800 | B1 | 6/2016 | Do et al. |
| 9,390,225 | B2 | 7/2016 | Barber et al. |
| 9,836,576 | B1 | 12/2017 | Do et al. |
| 9,864,835 | B2 | 1/2018 | Avey et al. |
| 11,113,609 | B2 | 9/2021 | Roy et al. |
| 2002/0019746 | A1 | 2/2002 | Rienhoff et al. |
| 2002/0143578 | A1 | 10/2002 | Cole et al. |
| 2003/0101000 | A1 | 5/2003 | Bader et al. |
| 2003/0113727 | A1 | 6/2003 | Girn et al. |
| 2003/0172065 | A1 | 9/2003 | Sorenson et al. |
| 2004/0083226 | A1 | 4/2004 | Eaton |
| 2004/0093334 | A1 | 5/2004 | Scherer |
| 2004/0126840 | A1 | 7/2004 | Cheng et al. |
| 2004/0267458 | A1 | 12/2004 | Judson et al. |
| 2005/0089852 | A1 | 4/2005 | Lee et al. |
| 2005/0147947 | A1* | 7/2005 | Cookson, Jr. ........... G06F 16/20 434/154 |
| 2005/0164704 | A1 | 7/2005 | Winsor |
| 2005/0164705 | A1 | 7/2005 | Rajkotia et al. |
| 2005/0192008 | A1 | 9/2005 | Desai et al. |
| 2007/0050354 | A1 | 3/2007 | Rosenberg |
| 2007/0260599 | A1 | 11/2007 | McGuire et al. |
| 2008/0040046 | A1* | 2/2008 | Chakraborty ........... G16B 20/40 702/20 |
| 2008/0081331 | A1 | 4/2008 | Myres et al. |
| 2008/0082955 | A1 | 4/2008 | Andreessen et al. |
| 2008/0111716 | A1 | 5/2008 | Artan et al. |
| 2008/0113727 | A1 | 5/2008 | Vallejo et al. |
| 2008/0154566 | A1 | 6/2008 | Myres et al. |
| 2008/0162510 | A1 | 7/2008 | Baio et al. |
| 2008/0243398 | A1 | 10/2008 | Rabinowitz et al. |
| 2008/0255768 | A1 | 10/2008 | Martin et al. |
| 2009/0030985 | A1 | 1/2009 | Yuan |
| 2009/0287660 | A1 | 11/2009 | Shinjo et al. |
| 2010/0199066 | A1 | 8/2010 | Artan et al. |
| 2010/0223281 | A1 | 9/2010 | Hon et al. |
| 2010/0256917 | A1 | 10/2010 | McVean et al. |
| 2010/0287213 | A1 | 11/2010 | Rolls et al. |
| 2012/0054190 | A1 | 3/2012 | Peters |
| 2012/0191903 | A1 | 7/2012 | Araki et al. |
| 2013/0085728 | A1 | 4/2013 | Tang et al. |
| 2013/0149707 | A1 | 6/2013 | Sorenson et al. |
| 2014/0067355 | A1 | 3/2014 | Noto et al. |
| 2014/0082568 | A1 | 3/2014 | Hulet et al. |
| 2014/0108527 | A1 | 4/2014 | Aravanis et al. |
| 2014/0194300 | A1 | 7/2014 | Song et al. |
| 2014/0278138 | A1* | 9/2014 | Barber .................. G06F 16/252 702/19 |
| 2015/0106115 | A1 | 4/2015 | Hu et al. |
| 2016/0070859 | A1 | 3/2016 | Ignatenko |
| 2016/0350479 | A1 | 12/2016 | Han et al. |
| 2017/0017752 | A1 | 1/2017 | Noto et al. |
| 2017/0213127 | A1 | 7/2017 | Duncan |
| 2017/0262577 | A1 | 9/2017 | Ball et al. |
| 2019/0361923 | A1 | 11/2019 | Joseph et al. |

OTHER PUBLICATIONS

Ball, C. et al., "Ancestry DNA Matching White Paper," Ancestry.com., 2016, [Online] [Retrieved Sep. 18, 2019], Retrieved from the internet, URL:<<https://www.ancestry.com/corporate/sites/default/files/AncestryDNA-Matching-White-Paper.pdf>>, Last updated Mar. 31, 2016, pp. 1-46.

Baran, Y. et al., "Fast and accurate inference of local ancestry in Latino populations." Bioinformatics, May 2012, vol. 28, No. 10, pp. 1359-1367.

Bastian, M. et al., "Gephi: an open source software for exploring and manipulating networks," Third international AAAI conference on weblogs and social media, May 2009, 361-362.

Bercovici, S. et al., "Ancestry inference in complex admixtures via variable-length Markov chain linkage models," Annual International Conference on Research in Computational Molecular Biology, Springer, Berlin, Heidelberg, Apr. 2012, vol. 7262, pp. 12-28.

Brisbin, A. et al. "PCAdmix: principal components-based assignment of ancestry along each chromosome in individuals with admixed ancestry from two or more populations," Human biology, Aug. 2012, vol. 84, No. 4, 343-364.

Browning, B.I. et al., "Detecting Identity by Descent and Estimating Genotype Error Rates in Sequence Data," The American Journal of Human Genetics, Nov. 7, 2013, pp. 840-851.

Browning, B.L., "A Fast, Powerful Method for Detecting Identity by Descent," The American Journal of Human Genetics, Feb. 11, 2011, vol. 88, pp. 173-182.

Browning, B.L., "A Unified Approach to Genotype Imputation and Haplotype-Phase Inference for Large Data Sets of Trios and Unrelated Individuals," The American Journal of Human Genetics, Feb. 13, 2009, vol. 84, pp. 210-223.

Browning, B.L et al., "Efficient Multilocus Association Testing for Whole Genome Association Studies Using Localized Haplotype Clustering," Genetic Epidemiology, vol. 31, Feb. 26, 2007, pp. 365-375.

Browning, B.L., "Genotype Imputation with Millions of Reference Samples," The American Journal of Human Genetics, Jan. 7, 2016, vol. 98, pp. 116-126.

Browning, S. R., "Rapid and Accurate Haplotype Phasing and Missing-Data Inference for Whole-Genome Association Studies by Use of Localized Haplotype Clustering," The American Journal of Human Genetics, Nov. 2007, vol. 81, 14 pages.

Browning, S.R. et al., "Haplotype phasing: Existing methods and new developments," Nat Rev Genet, Apr. 1, 2012, vol. 12, No. 10, pp. 703-714.

Browning, S.R., "Multilocus Association Mapping Using Variable-Length Markov Chains," The American Journal of Human Genetics, Jun. 2006, vol. 78, pp. 903-913.

Cann, H.M. et al., "A human genome diversity cell line panel," Science, Apr. 2002, vol. 296, No. 5566, pp. 261-262.

Cavalli-Sforza, L.L. "The human genome diversity project: past, present and future," Nature Reviews Genetics, Apr. 2005, vol. 6, No. 4.

De Roos, A.P.W., "Genomic selection in dairy cattle," PHD Thesis at Wageningen University, Jan. 2011, 185 pages.

Dudoit, et al., "A score test for the linkage analysis of qualitative and quantitative traits based on identity by descent data from sib-pairs," Biostatistics, vol. 1, Iss. 1, Mar. 2000, pp. 1-26.

Falush, D. et al., "Inference of Population Structure Using Multilocus Genotype Data: Linked Loci and Correlated Allele Frequencies," Genetics, vol. 164, Aug. 2003, pp. 1567-1587.

Ghahramani, Z. "An Introduction to Hidden Markov Models and Bayesian Networks," International Journal of Pattern recognition and Artificial Intelligence, Jun. 2001, vol. 15, No. 1, pp. 9-42.

Gravel, S., "Population genetics models of local ancestry," Genetics, Jun. 2012, vol. 191, No. 2, pp. 607-619.

Guan, Y. "Detecting structure of haplotypes and local ancestry," Genetics, Mar. 2014, vol. 196, No. 3, pp. 625-642.

Halperin, E. et al., "Haplotype reconstruction from genotype data using Imperfect Phylogeny," Bioinformatics, Aug. 2004, vol. 20, No. 12, pp. 1842-1849.

(56) References Cited

OTHER PUBLICATIONS

Han, E. et al., "Clustering of 770,000 genomes reveals post-colonial population structure of North America," Nature communications, Feb. 2017, vol. 8, pp. 1-12.

Harvard.edu, "Plink . . . Whole genome assocaition analysis toolset," [Online] [Retrieved Sep. 19, 2019], Last edited Jan. 25, 2017, Retrieved from the internet , URL:<<http://zzz.bwh.harvard.edu/plink/>>, 4 pages.

Hellenthal, G. et al., "A genetic atlas of human admixture history," Science, Feb. 2014, vol. 343, No. 6172, pp. 747-751.

Howie, B. N. et al., "A Flexible and Accurate Genotype Imputation Method for the Next Generation of Genome-Wide Association Studies," PLoS Genetics, Jun. 2009, vol. 5, No. 6, pp. 1-15.

International HapMap Consortium, "A haplotype map of the human genome," Nature, Oct. 2005, vol. 437, No. 27, pp. 1299-1320.

International HapMap Consortium, "A second generation human haplotype map of over 3.1 million SNPs," Nature, Oct. 2007, vol. 449, No. 7164, pp. 1-30.

Itan, Y. et al., "The origins of lactase persistence in Europe," PLoS computational biology, Aug. 2009, vol. 5, No. 8, pp. 1-13.

Jarvis, J.P. et al., "Patterns of Ancestry of Natural Selection and Genetic Association with Stature in Western African Pygmies," PLoS Genetics, vol. 8, Iss. 4, Apr. 26, 2012, pp. 1-15.

Ke, X. et al. "Singleton SNPs in the human genome and implications for genome-wide association studies," European Journal of Human Genetics, Jan. 2008, vol. 16, No. 4, 10 pages.

Lawson, D.J. et al., "Inference of population structure using dense haplotype data," PLoS genetics, Jan. 2012, vol. 8, No. 1, pp. 1-16.

Li, N. et al., "Modeling Linkage disequilibrium and Identifying Recombination Hotspots Using Single-Nucleotide Polymorphism Data," the Genetics Society of America, Dec. 2003, vol. 165, pp. 2213-2233.

Li, Y. et al., "MaCH: Using Sequence and Genotype Data to Estimate haplotypes and Unobserved Genotypes," Genetic Epidemiology, Dec. 2010, vol. 34, pp. 816-834.

Loh, P.R. et al., "Inferring admixture histories of human populations using linkage disequilibrium," Genetics, Apr. 2013, vol. 193, No. 4, pp. 1233-1254.

Ma, P. et al., "Comparison of different methods for imputing genome-wide marker genotypes in Swedish and Finnish Red Cattle," J. Dairy Sci., Jul. 2013, vol. 96, pp. 4666-4677.

Ma, Y. et al. "Accurate inference of local phased ancestry of modern admixed populations," Scientific reports, Jul. 2014, vol. 4, No. 5800 , pp. 1-5.

Maples, B.K. et al., "RFMix: a discriminative modeling approach for rapid and robust local-ancestry inference," The American Journal of Human Genetics, Aug. 2013, vol. 93, No. 2, pp. 278-288.

McPeek, M. S. et al., "Assessment of Linkage Disequilibrium by the Decay of Haplotype Sharing with Application to Fine-Scale Genetic Mapping," American Journal of Human Genetics, Sep. 1999, vol. 65, pp. 858-875.

Moreno-Estrada, A. et al., Reconstructing the Population Genetic History of the Caribbean, PLOS Genetics, Nov. 2013, vol. 9, No. 11, pp. 1-19.

Morrison, A.C. et al., "Prediction of Coronary Heart Disease Risk using a Genetic Risk Score: The Atherosclerosis Risk in Communities Study," American Journal of Epidemiology, vol. 166, No. 1, Apr. 18, 2007, pp. 28-35.

Noto, K. et al., "A novel approach for estimating local and global admicture proportion based on rich haplotype models," Invited Talk at the American Society of Human Genetics (ASHG) annual meeting, Baltimore, MD, Oct. 2015, 6 pages.

Noto, K. et al., Abstract, "322 Polly: A novel approach for estimating local and global admixture proportion based on rich haplotype models," ASHG 2015 Abstracts, The American Society of Human Genetics 65th Annual Meeting, Oct. 2015, 184 pages.

Noto, K., et al. "Underdog: a fully-supervised phasing algorithm that learns from hundreds of thousands of samples and phases in minutes. Invited Talk," 64th Annual Meeting of the American Society of Human Genetics, 2014, pp. 1-19 . . . .

Palin, K. et al., "Identity-by-Descent-Based Phasing and Imputation in Founder Populations Using Graphical Models," Genetic Epidemiology, vol. 35, Oct. 17, 2011, pp. 853-860.

Paşaniuc, B. et al., "Imputation-based local ancestry inference in admixed populations," International Symposium on Bioinformatics Research and Applications, Springer, Berlin, Heidelberg, May 2009, pp. 221-233.

Paşaniuc, B.et al. "Inference of locus-specific ancestry in closely related populations," Bioinformatics, May 2009, vol. 25, No. 12, pp. i213-i221.

Patterson, N. et al., "Population structure and eigenanalysis," PLoS genetics, Dec. 2006, vol. 2, No. 12, pp. 2074-2093.

PCT International Search Report and Written Opinion, PCT Patent Application No. PCT/1B2019/057667, Jan. 10, 2020, 10 pages.

PCT International Search Report and Written Opinion, PCT Patent Application No. PCT/1B2020/062256, Mar. 22, 2021, 14 pages.

Platt, J.C., "Probabilistic Outputs for Support Vector Machines and Comparisons to Regularized Likelihood Methods," Mar. 26, 1999, pp. 1-11.

Price, A.L. et al., "Sensitive Detection of Chromosomal Segments of Distinct Ancestry in Admixed Populations," PLoS Genetics, vol. 5, Iss. 6, Jun. 2009, pp. 1-18.

Pritchard, J.K. et al., "Inference of population structure using multilocus genotype data," Genetics Society of America, Jun. 2000, vol. 155, No. 2, pp. 945-959.

Purcell, S. et al., "PLINK: a tool set for whole-genome association and population-based linkage analyses," The American journal of human genetics, Sep. 2007, vol. 81, No. 3, pp. 559-575.

Qian, Y. et al., "Efficient clustering of identity-by-descent between multiple individuals," Bioinformatics, vol. 30, No. 7, Dec. 19, 2013, pp. 915-922.

Rabiner, L.R., "A Tutorial on Hidden Markov Models and Selected Applications in Speech Recognition," Proceedings of the IEEE, Feb. 1989, vol. 77, No. 2, pp. 257-286.

Ranciaro, A. et al., "Genetic origins of lactase persistence and the spread of pastoralism in Africa," The American Journal of Human Genetics, Apr. 2014, vol. 94, No. 4, pp. 496-510.

Roach, J.C. et al., "Analysis of genetic inheritance in a family quartet by whole-genome sequencing," Science, Apr. 2010, vol. 328, No. 5978, pp. 636-639.

Ron, D., "On the Learnability and Usage of Acyclic Probabilistic Finite Automata," Journal of Computer and System Sciences, Apr. 1998, vol. 56, pp. 133-152.

Sankararaman, S. et al., "Estimating local ancestry in admixed populations," The American Journal of Human Genetics, Feb. 2008, vol. 82, No. 2, pp. 290-303.

Scheet, P. et al., "A Fast and Flexible Statistical model for Large-Scale Population Genotype Data: Applications to Inferring Missing Genotypes and Hplotypic Phase," The American Journal of Human Genetics, Apr. 2006, vol. 78, pp. 629-644.

Seligsohn, U. et al., "Genetic Susceptibility to Venous Thrombosis," The New England Journal of Medicine, vol. 344, No. 16, Apr. 19, 2001, pp. 1222-1231.

Staples, J. et al., "PRIMUS: Rapid Reconstruction of Pedigrees from Genome-wide Estimates of Identity by Descent," The American Journal of Human Genetics, vol. 95, Nov. 6, 2014, pp. 553-564.

Stephens, M. et al., "Accounting for Decay of Linkage Disequilibrium in Haplotype Inference and Missing-Data Imputation," American Journal of Human Genetics, Mar. 2005, vol. 76, pp. 449-462.

Sturm, R.A. et al., "A single SNP in an evolutionary conserved region within intron 86 of the HERC2 gene determines human blue-brown eye color," The American Journal of Human Genetics, Feb. 2008, vol. 82, No. 2, pp. 424-431.

Sundquist, A. et al., "Effect of genetic divergence in identifying ancestral origin using HAPAA," Genome Res., Mar. 18, 2008, vol. 18, pp. 676-682.

Tang, H. et al., "Reconstructing Genetic Ancestry Blocks in Admixed Individuals," The American journal of Human Genetics, Jul. 2006, vol. 79, pp. 1-12.

The 1000 Genomes Project Consortium, "A global reference for human genetic variation," Macmillan Publishers Limited, Nature, Oct. 1, 2015, vol. 526, No. 7571, pp. 68-74.

(56) References Cited

OTHER PUBLICATIONS

The International HAPMAP 3 Consortium, "Integrating common and rare genetic variation in diverse human populations," Nature, vol. 467, Sep. 2, 2010, pp. 52-58.
Tipping, M.E., "Sparse Bayesian Learning and the Relevance Vector Machine," Journal of Machine Learning Research, Jun. 2001, pp. 211-244.
U.S. Appl. No. 61/724,228, filed Nov. 8, 2012, Inventor Chuong Do.
U.S. Appl. No. 61/724,236, filed Nov. 8, 2012, Inventor Chuong Do.
Visscher, P.M. et al., "Heritability in the genomics era-concepts and misconceptions," Nature Reviews Genetics, Mar. 4, 2008, pp. 255-266.
Weedon, M.N. et al., "Combining Information from Common Type 2 Diabetes Risk Polymorphisms Improves Disease Prediction," PLoS Med., vol. 3, Iss. 10, Oct. 2006, pp. 1877-1882.
Wikipedia, "Inverse distance weighting," [Online] [Retrieved Sep. 18, 2019], Last edited Mar. 4, 2019, Retrieved from the internet ,URL:<<https://en.wikipedia.org/wiki/Inverse_distance_weighting>>.
Williams, A.L. et al., "Phasing of Many Thousands of Genotyped Samples," The American Journal of Human Genetics, Aug. 10, 2012, vol. 91, pp. 238-251.
Yang, Q. et al., "Improving the Prediction of Complex Diseases by Testing for Multiple Disease-Susceptibility Genes," American Journal of Human Genetics, vol. 72, Feb. 14, 2003, pp. 636-649.
Yoon, B.J., "Hidden Markov Models and their Applications in Biological Sequence Analysis," Current Genomics, Nov. 2009, vol. 10, pp. 402-415.
Zhao, H. et al., "Haplotype analysis in population genetics and association studies," Pharmacogenomics, Mar. 2003, vol. 4, No. 2, pp. 171-178.
U.S. Appl. No. 17/128,009, filed Dec. 24, 2021, 16 pages.

\* cited by examiner

LINKING INDIVIDUAL DATASETS TO A DATABASE

CROSS-REFERENCE TO RELATED APPLICATIONS

The present application is a continuation of U.S. application Ser. No. 17/128,009, filed on Dec. 19, 2020, which claims the benefit of U.S. Provisional Patent Application No. 62/951,646 filed on Dec. 20, 2019. All of which are hereby incorporated by reference in their entirety.

FIELD

The disclosed embodiments relate to linking individual datasets to a database.

BACKGROUND

A large-scale database such as user profile and genetic database can include billions of data records. This type of database may allow users to build family trees, research their family history, and make meaningful discoveries about the lives of their ancestors. Users may try to identify relatives with datasets in the database. However, identifying relatives in the sheer amount of data is not a trivial task. Datasets associated with different individuals may not be connected without a proper determination of how the datasets are related. Comparing a large number of datasets without a concrete strategy may also be computational infeasible because each dataset may also include a large number of data bits. Given an individual dataset and a database with datasets that are potentially related to the individual dataset, it is often challenging to identify a dataset in the database to that is associated with the individual dataset.

SUMMARY

The system disclosed herein relates to example embodiments that link an individual dataset to a database. The system first receives a target individual dataset associated with a target individual. Candidate individual datasets that are potentially related to the target individual dataset are then identified. A related individual dataset is identified from the candidate individual datasets where the related individual dataset has data bits that match a portion of data bits in the target individual dataset. The system then identifies a group of parent nodes that are common parent nodes to both the related individual dataset and the target individual dataset and retrieves a group of data trees that the parent nodes belong to. The data trees contain information describing inter-relationships among datasets in the data tree. A data tree of the group of data trees is selected and a position in the data tree is identified to assign the target individual dataset based on strings of matched data bits and number of the matched strings between the target individual dataset and the datasets in the data tree.

In yet another embodiment, a non-transitory computer readable medium that is configured to store instructions is described. The instructions, when executed by one or more processors, cause the one or more processors to perform a process that includes steps described in the above computer-implemented methods or described in any embodiments of this disclosure. In yet another embodiment, a system may include one or more processors and a storage medium that is configured to store instructions. The instructions, when executed by one or more processors, cause the one or more processors to perform a process that includes steps described in the above computer-implemented methods or described in any embodiments of this disclosure.

The figures depict various embodiments for purposes of illustration only. One skilled in the art will readily recognize from the following discussion that alternative embodiments of the structures and methods illustrated herein may be employed without departing from the principles described herein.

DETAILED DESCRIPTION

The figures (FIGs.) and the following description relate to preferred embodiments by way of illustration only. One of skill in the art may recognize alternative embodiments of the structures and methods disclosed herein as viable alternatives that may be employed without departing from the principles of what is disclosed.

Reference will now be made in detail to several embodiments, examples of which are illustrated in the accompanying figures. It is noted that wherever practicable similar or like reference numbers may be used in the figures and may indicate similar or like functionality. The figures depict embodiments of the disclosed system (or method) for purposes of illustration only. One skilled in the art will readily recognize from the following description that alternative embodiments of the structures and methods illustrated herein may be employed without departing from the principles described herein.

Example System Environment

Figure 1:
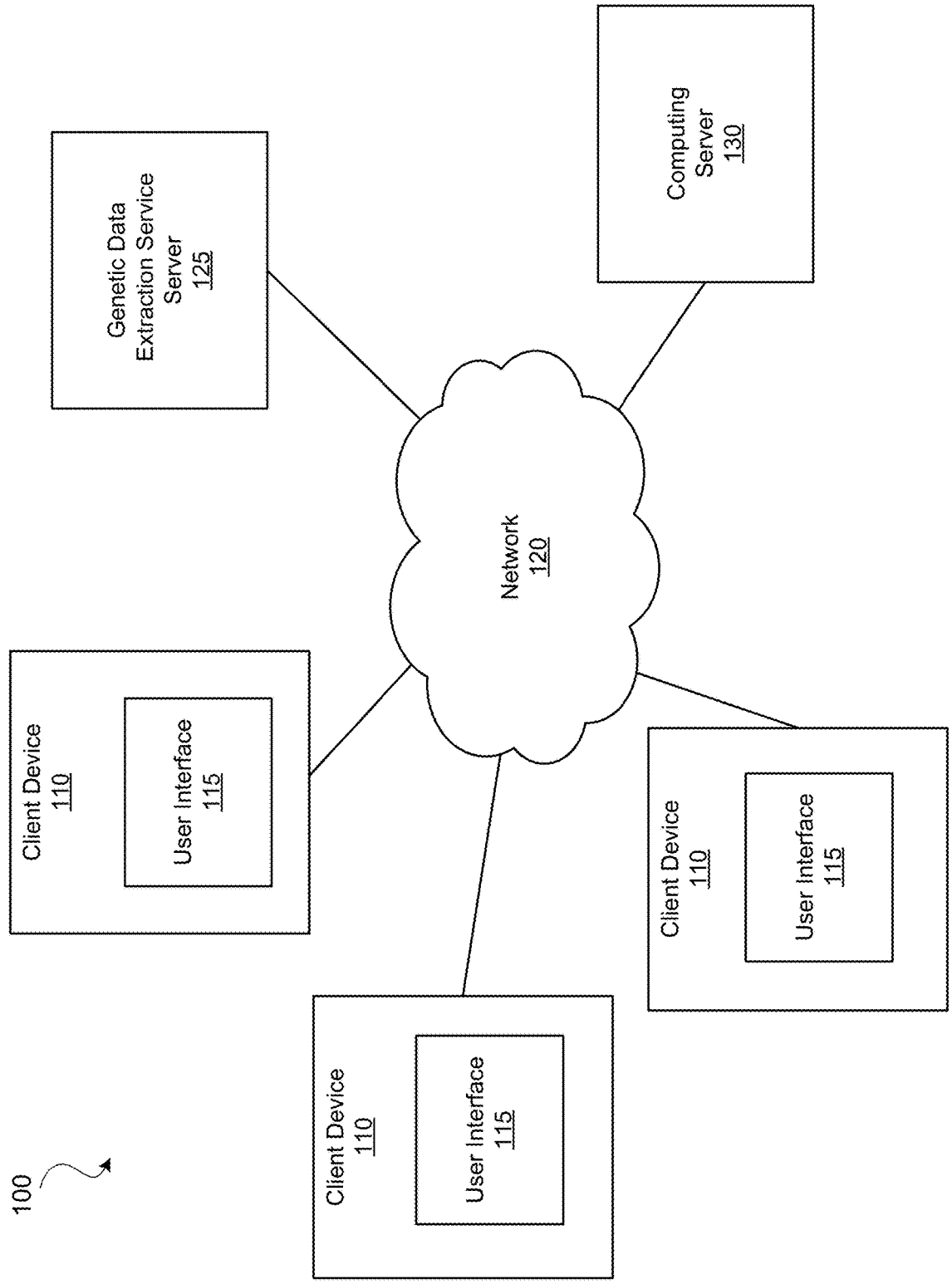
FIG. 1 illustrates a diagram of a system environment of an example computing system, in accordance with an embodiment.

FIG. 1 illustrates a diagram of a system environment 100 of an example computing server 130, in accordance with an embodiment. The system environment 100 shown in FIG. 1 includes one or more client devices 110, a network 120, a genetic data extraction service server 125, and a computing server 130. In various embodiments, the system environment 100 may include fewer or additional components. The system environment 100 may also include different components.

The client devices 110 are one or more computing devices capable of receiving user input as well as transmitting and/or receiving data via a network 120. Example computing devices include desktop computers, laptop computers, personal digital assistants (PDAs), smartphones, tablets, wearable electronic devices (e.g., smartwatches), smart household appliance (e.g., smart televisions, smart speakers, smart home hubs), Internet of Things (IoT) devices or other suitable electronic devices. A client device 110 communicates to other components via the network 120. Users may be customers of the computing server 130 or any individuals who access the system of the computing server 130, such as an online website or a mobile application. In one embodiment, a client device 110 executes an application that launches a graphical user interface (GUI) for a user of the client device 110 to interact with the computing server 130. The GUI may be an example of a user interface 115. A client device 110 may also execute a web browser application to enable interactions between the client device 110 and the computing server 130 via the network 120. In another embodiment, the user interface 115 may take the form of a software application published by the computing server 130 and installed on the user device 110. In yet another embodiment, a client device 110 interacts with the computing server 130 through an application programming interface (API) running on a native operating system of the client device 110, such as IOS or ANDROID.

The network 120 provides connections to the components of the system environment 100 through one or more subnetworks, which may include any combination of local area and/or wide area networks, using both wired and/or wireless communication systems. In one embodiment, a network 120 uses standard communications technologies and/or protocols. For example, a network 120 may include communication links using technologies such as Ethernet, 802.11, worldwide interoperability for microwave access (WiMAX), 3G, 4G, Long Term Evolution (LTE), 5G, code division multiple access (CDMA), digital subscriber line (DSL), etc. Examples of network protocols used for communicating via the network 120 include multiprotocol label switching (MPLS), transmission control protocol/Internet protocol (TCP/IP), hypertext transport protocol (HTTP), simple mail transfer protocol (SMTP), and file transfer protocol (FTP). Data exchanged over a network 120 may be represented using any suitable format, such as hypertext markup language (HTML) or extensible markup language (XML). In some embodiments, all or some of the communication links of a network 120 may be encrypted using any suitable technique or techniques such as secure sockets layer (SSL), transport layer security (TLS), virtual private networks (VPNs), Internet Protocol security (IPsec), etc. The network 120 also includes links and packet switching networks such as the Internet.

Individuals, who may be customers of a company operating the computing server 130, provide biological samples for analysis of their genetic data. Individuals may also be referred to as users. In one embodiment, an individual uses a sample collection kit to provide a biological sample (e.g., saliva, blood, hair, tissue) from which genetic data is extracted and determined according to nucleotide processing techniques such as amplification and sequencing. Amplification may include using polymerase chain reaction (PCR) to amplify segments of nucleotide samples. Sequencing may include sequencing of deoxyribonucleic acid (DNA) sequencing, ribonucleic acid (RNA) sequencing, etc. Suitable sequencing techniques may include Sanger sequencing and massively parallel sequencing such as various next-generation sequencing (NGS) techniques including whole genome sequencing, pyrosequencing, sequencing by synthesis, sequencing by ligation, and ion semiconductor sequencing. In one embodiment, a set of SNPs (e.g., 300,000) that are shared between different array platforms (e.g., Illumina OmniExpress Platform and Illumina HumanHap 650Y Platform) may be obtained as the genetic data. Genetic data extraction service server 125 receives biological samples from users of the computing server 130. The genetic data extraction service server 125 performs sequencing of the biological samples and determines the base pair sequences of the individuals. The genetic data extraction service server 125 generates the genetic data of the individuals based on the sequencing results. The genetic data may include data sequenced from DNA or RNA and may include base pairs from coding and/or noncoding regions of DNA.

The genetic data may take different forms and include information regarding various biomarkers of an individual. For example, in one embodiment, the genetic data may be the base pair sequence of an individual. The base pair sequence may include the whole genome or a part of the genome such as certain genetic loci of interest. In another embodiment, the genetic data extraction service server 125 may determine genotypes from sequencing results, for example by identifying genotype values of single nucleotide polymorphisms (SNPs) present within the DNA. The results in this example may include a sequence of genotypes corresponding to various SNP sites. A SNP site may also be referred to as a SNP loci. A genetic locus is a segment of a genetic sequence. A locus can be a single site or a longer stretch. The segment can be a single base long or multiple bases long. In one embodiment, the genetic data extraction service server 125 may perform data pre-processing of the genetic data to convert raw sequences of base pairs to sequences of genotypes at target SNP sites. Since a typical human genome may differ from a reference human genome at only several million SNP sites (as opposed to billions of base pairs in the whole genome), the genetic data extraction service server 125 may extract only the genotypes at a set of target SNP sites and transmit the extracted data to the computing server 130 as the genetic dataset of an individual. SNPs, base pair sequence, genotype, haplotype, RNA sequences, protein sequences, phenotypes are examples of biomarkers.

The computing server 130 performs various analyses of the genetic data, genealogical data, and users' survey responses to generate results regarding the phenotypes and genealogy of users of computing server 130. Depending on the embodiments, the computing server 130 may also be referring to as an online server, a personal genetic service server, a genealogy server, a family tree building server, and/or a social networking system. The computing server 130 receives genetic data from the genetic data extraction service server 125 and stores the genetic data in the data store of the computing server 130. The computing server 130 may analyze the data to generate results regarding the genetics or genealogy of users. The results regarding the genetics or genealogy of users may include the ethnicity compositions of users, paternal and maternal genetic analysis, identification or suggestion of potential family relatives, ancestor information, analyses of DNA data, potential or identified traits such as phenotypes of users (e.g., diseases, appearance traits, other genetic characteristics, and other non-genetic characteristics including social characteristics), etc. The computing server 130 may present or cause the user interface 115 to present the results to the users through a GUI displayed at the client device 110. The results may include graphical elements, textual information, data, charts, and other elements such as family trees In one embodiment, the computing server 130 also allows various users to create one or more genealogical profiles of the user. The genealogical profile may include a list of individuals (e.g., ancestors, relatives, friends, and other people of interest) who are added or selected by the user or suggested by the computing server 130 based on the genealogical records and/or genetic records. The user interface 115 controlled by or in communication with the computing server 130 may display the individuals in a list or as a family tree such as in the form of a pedigree chart. In one embodiment, subject to user's privacy setting and authorization, the computing server 130 may allow information generated from the user's genetic dataset to be linked to the user profile and to one or more of the family trees. The users may also authorize the computing server 130 to analyze their genetic dataset and allow their profiles to be discovered by other users.

Example Computing Server Architecture

Figure 2:
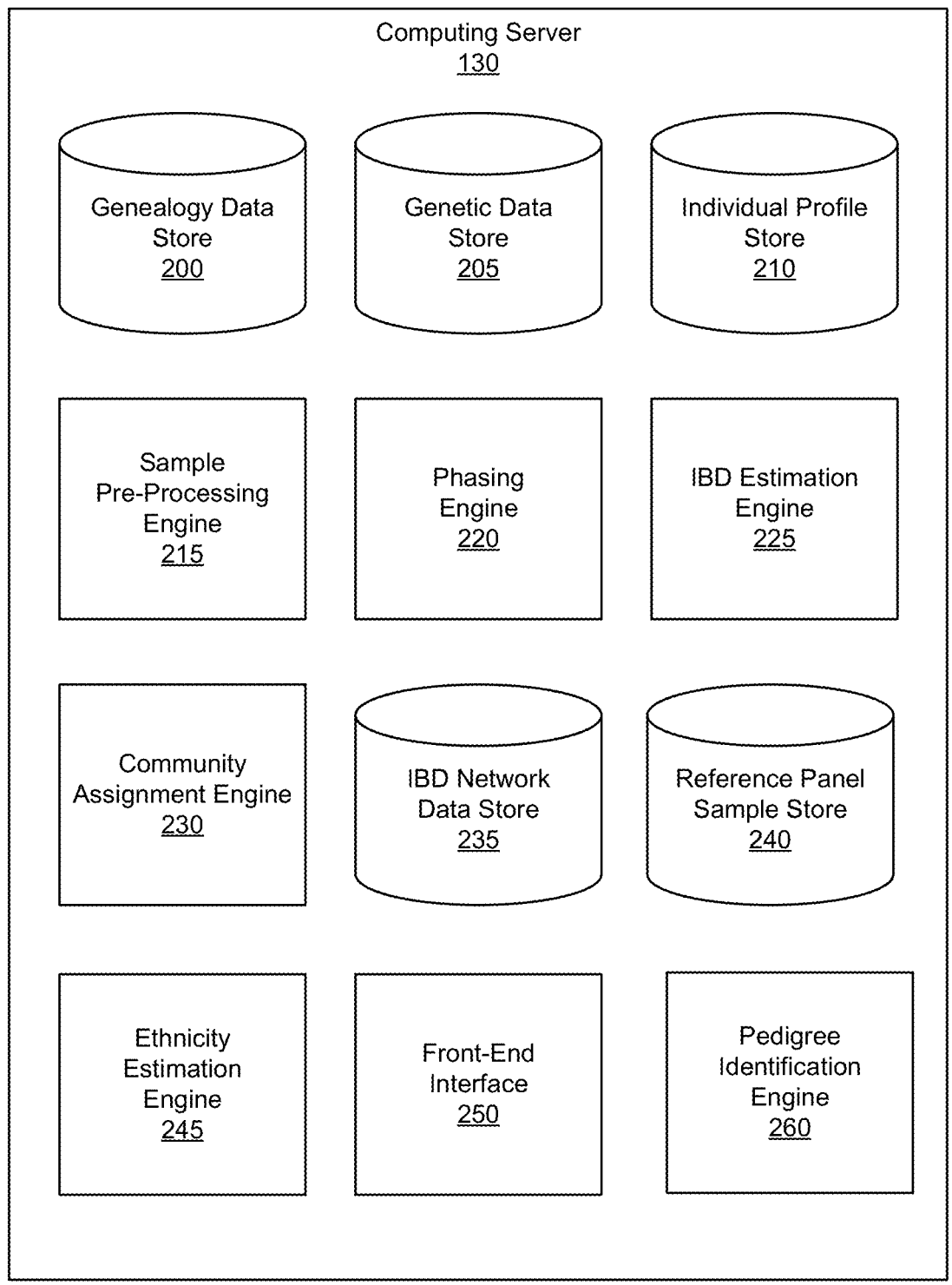
FIG. 2 is a block diagram of an architecture of an example computing system, in accordance with an embodiment.

FIG. 2 is a block diagram of an architecture of an example computing server 130, in accordance with an embodiment. In the embodiment shown in FIG. 2, the computing server 130 includes a genealogy data store 200, a genetic data store 205, an individual profile store 210, a sample pre-processing engine 215, a phasing engine 220, an identity by descent (IBD) estimation engine 225, a community assignment engine 230, an IBD network data store 235, a reference panel sample store 240, an ethnicity estimation engine 245, and a front-end interface 250. The functions of the computing server 130 may be distributed among the elements in a different manner than described. In various embodiments, the computing server 130 may include different components and fewer or additional components. Each of the various data stores may be a single storage device, a server controlling multiple storage devices, or a distributed network that is accessible through multiple nodes (e.g., a cloud storage system).

The computing server 130 stores various data of different individuals, including genetic data, genealogical data, and survey response data. The computing server 130 processes the genetic data of users to identify shared identity-by-descent (IBD) segments between individuals. The genealogical data and survey response data may be part of user profile data. The amount and type of user profile data stored for each user may vary based on the information of a user, which is provided by the user as she creates an account and profile at a system operated by the computing server 130 and continues to build her profile, family tree, and social network at the system and to link her profile with her genetic data. Users may provide data via the user interface 115 of a client device 110. Initially and as a user continues to build her genealogical profile, the user may be prompted to answer questions related to basic information of the user (e.g., name, date of birth, birthplace, etc.) and later on more advanced questions that may be useful for obtaining additional genealogical data. The computing server 130 may also include survey questions regarding various traits of the users such as the users' phenotypes, characteristics, preferences, habits, lifestyle, environment, etc.

Genealogical data may be stored in the genealogical data store 200 and may include various types of data that are related to tracing family relatives of users. Examples of genealogical data include names (first, last, middle, suffixes), gender, birth locations, date of birth, date of death, marriage information, spouse's information kinships, family history, dates and places for life events (e.g., birth and death), other vital data, and the like.

In some instances, family history can take the form of a pedigree of an individual (e.g., the recorded relationships in the family). The family tree information associated with an individual may include one or more specified nodes. Each node in the family tree represents the individual, an ancestor of the individual who might have passed down genetic material to the individual, and the individual's other relatives including siblings, cousins, offspring in some cases. Genealogical data may also include connections and relationships among users of the computing server 130. The information related to the connections among a user and her relatives that may be associated with a family tree may also be referred to as pedigree data or family tree data.

In addition to user-input data, genealogical data may also take other forms that are obtained from various sources such as public records and third-party data collectors. For example, genealogical records from public sources include birth records, marriage records, death records, census records, court records, probate records, adoption records, obituary records, etc. Likewise, genealogical data may include data from one or more of a pedigree of an individual, the Ancestry World Tree system, a Social Security Death Index database, the World Family Tree system, a birth certificate database, a death certificate database, a marriage certificate database, an adoption database, a draft registration database, a veterans database, a military database, a property records database, a census database, a voter registration database, a phone database, an address database, a newspaper database, an immigration database, a family history records database, a local history records database, a business registration database, a motor vehicle database, and the like.

Furthermore, the genealogical data store 200 may also include relationship information inferred from the genetic data stored in the genetic data store 205 and information received from the individuals. For example, the relationship information may indicate which individuals are genetically related, how they are related, how many generations back they share common ancestors, lengths and locations of IBD segments shared, which genetic communities an individual is a part of, variants carried by the individual, and the like.

The computing server 130 maintains genetic datasets of individuals in the genetic data store 205. A genetic dataset of an individual may be a digital dataset of nucleotide data (e.g., SNP data) and corresponding metadata. A genetic dataset may contain data of the whole or portions of an individual's genome. The genetic data store 205 may store a pointer to a location associated with the genealogical data store 200 associated with the individual. A genetic dataset may take different forms. In one embodiment, a genetic dataset may take the form of a base pair sequence of the sequencing result of an individual. A base pair sequence dataset may include the whole genome of the individual (e.g., obtained from a whole-genome sequencing) or some parts of the genome (e.g., genetic loci of interest).

In another embodiment, a genetic dataset may take the form of sequences of genetic markers. Examples of genetic markers may include target SNP loci (e.g., allele sites) filtered from the sequencing results. A SNP locus that is single base pair long may also be referred to as a SNP site. A SNP locus may be associated with a unique identifier. The genetic dataset may be in a form of a diploid data that includes a sequencing of genotypes, such as genotypes at the target SNP loci, or the whole base pair sequence that includes genotypes at known SNP loci and other base pair sites that are not commonly associated with known SNPs. The diploid dataset may be referred to as a genotype dataset or a genotype sequence. Genotype may have a different meaning in various contexts. In one context, an individual's genotype may refer to a collection of diploid alleles of an individual. In other contexts, a genotype may be a pair of alleles present on two chromosomes for an individual at a given genetic marker such as a SNP site.

A genotype at a SNP site may include a pair of alleles. The pair of alleles may be homozygous (e.g., A-A or G-G) or heterozygous (e.g., A-T, C-T). Instead of storing the actual nucleotides, the genetic data store 205 may store genetic data that are converted to bits. For a given SNP site, oftentimes only two nucleotide alleles (instead of all 4) are observed. As such, a 2-bit number may represent a SNP site. For example, 00 may represent homozygous first alleles, 11 may represent homozygous second alleles, and 01 or 10 may represent heterozygous alleles. A separate library may store what nucleotide corresponds to the first allele and what nucleotide corresponds to the second allele at a given SNP site.

A diploid dataset may also be phased into two sets of haploid data, one corresponding to a first parent side and another corresponding to a second parent side. The phased datasets may be referred to as haplotype datasets or haplotype sequences. Similar to genotype, haplotype may have a different meaning in various contexts. In one context, a haplotype may also refer to a collection of alleles that corresponds to a genetic segment. In other contexts, a haplotype may refer to a specific allele at a SNP site. For example, a sequence of haplotypes may refer to a sequence of alleles of an individual that are inherited from a parent.

The individual profile store 210 stores profiles and related metadata associated with various individuals appeared in the computing server 130. A computing server 130 may use unique individual identifiers to identify various users and other non-users that might appear in other data sources such as ancestors or historical persons who appear in any family tree or genealogical database. A unique individual identifier may a hash of certain identification information of an individual, such as a user's account name, user's name, date of birth, location of birth, or any suitable combination of the information. The profile data related to an individual may be stored as metadata associated with an individual's profile. For example, the unique individual identifier and the metadata may be stored as a key-value pair using the unique individual identifier as a key.

An individual's profile data may include various kinds of information related to the individual. The metadata about the individual may include one or more pointer associating genetic datasets such as genotype and phased haplotype data of the individual that are saved in the genetic data store 205. The metadata about the individual may also individual information related to family trees and pedigree datasets that include the individual. The profile data may further include declarative information about the user that was authorized by the user to be shared and may also include information inferred by the computing server 130. Other examples of information stored in a user profile may include biographic, demographic, and other types of descriptive information such as work experience, educational history, gender, hobbies, or preferences, location and the like. In one embodiment, the user profile data may also include one or more photos of the users and photos of relatives (e.g., ancestors) of the users that are uploaded by the users. A user may authorize the computing server 130 to analyze one or more photos to extract information, such as user's or relative's appearance traits (e.g., blue eyes, curved hair, etc.), from the photos. The appearance traits and other information extracted from the photos may also be saved in the profile store. In some cases, the computing server may allow users to upload many different photos of the users, their relatives, and even friends. User profile data may also be obtained from other suitable sources, including historical records (e.g., records related to an ancestor), medical records, military records, photographs, other records indicating one or more traits, and other suitable recorded data.

For example, the computing server 130 may present various survey questions to its users from time to time. The responses to the survey questions may be stored at individual profile store 210. The survey questions may be related to various aspects of the users and the users' families. Some survey questions may be related to users' phenotypes, while other questions may be related to environmental factors of the users.

Survey questions may concern health or disease-related phenotypes, such as questions related to the presence or absence of genetic diseases or disorders, inheritable diseases or disorders, or other common diseases or disorders that have family history as one of the risk factors, questions regarding any diagnosis of increased risk of any diseases or disorders, and questions concerning wellness-related issues such as family history of obesity, family history of causes of death, etc. The diseases identified by the survey questions may be related to single-gene diseases or disorders that are caused by a single-nucleotide variant, an insertion, or a deletion. The diseases identified by the survey questions may also be multifactorial inheritance disorders that may be caused by a combination of environmental factors and genes. Examples of multifactorial inheritance disorders may include heart disease, Alzheimer's diseases, diabetes, cancer, and obesity. The computing server 130 may obtain data of a user's disease-related phenotypes from survey questions of health history of the user and her family and also from health records uploaded by the user.

Survey questions also may be related to other types of phenotypes such as appearance traits of the users. A survey regarding appearance traits and characteristics may include questions related to eye color, iris pattern, freckles, chin types, finger length, dimple chin, earlobe types, hair color, hair curl, skin pigmentation, susceptibility to skin burn, bitter taste, male baldness, baldness pattern, presence of unibrow, presence of wisdom teeth, height, and weight. A survey regarding other traits also may include questions related to users' taste and smell such as the ability to taste bitterness, asparagus smell, cilantro aversion, etc. A survey regarding traits may further include questions related to users' body conditions such as lactose tolerance, caffeine consumption, malaria resistance, norovirus resistance, muscle performance, alcohol flush, etc. Other survey questions regarding a person's physiological or psychological traits may include vitamin traits and sensory traits such as ability to sense an asparagus metabolite. Traits may also be collected from historical records, electronic health records and electronic medical records.

The computing server 130 also may present various survey questions related to environmental factors of users. In this context, an environmental factor may be a factor that is not directly connected to the genetics of the users. Environmental factors may include users' preferences, habits, and lifestyle. For example, a survey regarding users' preferences may include questions related to things and activities that users like or dislike, such as types of music a user enjoys, dancing preference, party-going preference, certain sports that a user plays, video games preferences, etc. Other questions may be related to the users' diet preference such as like or dislike a certain type of food (e.g., ice cream, egg). A survey related to habits and lifestyle may include questions regarding smoking habits, alcohol consumption and frequency, daily exercise duration, sleeping habits (e.g., morning person versus night person), sleeping cycles and problems, hobbies, and travel preferences. Additional environmental factors may include diet amount (calories, macronutrients), physical fitness abilities (e.g. stretching, flexibility, heart rate recovery), family type (adopted family or not, has siblings or not, lived with extended family during childhood), property and item ownership (has home or rents, has smartphone or doesn't, has car or doesn't).

Surveys also may be related to other environmental factors such as geographical, social-economic, or cultural factors. Geographical questions may include questions related to the birth location, family migration history, town, or city of users' current or past residence. Social-economic questions may be related to users' education level, income, occupations, self-identified demographic groups, etc. Questions related to culture may concern users' native language, language spoken at home, customs, dietary practices, etc. Other questions related to users' cultural and behavioral questions are also possible.

For any survey questions asked, the computing server 130 may also ask an individual the same or similar questions regarding the traits and environmental factors of the ancestors, family members, other relatives or friends of the individual. For example, a user may be asked about the native language of the user and the native languages of the user's parents and grandparents. A user may also be asked about the health history of his or her family members.

In addition to storing the survey data in the individual profile store 210, the computing server 130 may store some responses that correspond to data related to genealogical and genetics respectively to genealogical data store 200 and genetic data store 205.

The user profile data, photos of users, survey response data, the genetic data, and the genealogical data may subject to the privacy and authorization setting from the users to specify any data related to the users can be accessed, stored, obtained, or otherwise used. For example, when presented with a survey question, a user may select to answer or skip the question. The computing server 130 may present users from time to time information regarding users' selection of the extent of information and data shared. The computing server 130 also may maintain and enforce one or more privacy settings for users in connection with the access of the user profile data, photos, genetic data, and other sensitive data. For example, the user may pre-authorize the access of the data and may change the setting as wish. The privacy settings also may allow a user to specify (e.g., by opting out, by not opting in) whether the computing server 130 may receive, collect, log, or store particular data associated with the user for any purpose. A user may restrict her data at various levels. For example, in one level, the data may not be accessed by the computing server 130 for purposes other than displaying the data in the user's own profile. On another level, the user may authorize anonymization of her data and participate in studies and researches conducted by the computing server 130 such as a large scale genetic study. In yet another level, the user may turn some portions of her genealogical data public to allow the user to be discovered by other users (e.g., potential relatives) and be connected in one or more family trees. Access or sharing of any information or data in the computing server 130 may also be subject to one or more similar privacy policies. A user's data and content objects in the computing server 130 may also be associated with different levels of restriction. The computing server 130 may also provide various notification feature to inform and remind users of their privacy and access settings. For example, when privacy settings for a data entry allow a particular user or other entities to access the data, the data may be described as being "visible," "public," or other suitable labels, in contrary to a "private" label.

In some cases, the computing server 130 may have a heightened privacy protection on certain types of data and data related to certain vulnerable groups. In some cases, the heightened privacy settings may strictly prohibit the use, analysis, sharing of data related to a certain vulnerable group. In other cases, the heightened privacy settings may specify that data subject to those settings require prior approval for access, publication, or other use. In some cases, the computing server 130 may provide the heightened privacy as a default setting for certain types of data, such as genetic data or any data that the user marks as sensitive. The user may opt in for sharing of those data or change the default privacy settings. In other cases, the heightened privacy settings may apply across the board for all data of certain groups of users. For example, if the computing server 130 determines that the user is a minor or has recognized that a picture of a minor is uploaded, the computing server 130 may designate all profile data associated with the minor as sensitive. In those cases, the computing server 130 may have one or more extra steps in seeking and confirming any sharing or use of the sensitive data.

The sample pre-processing engine 215 receives and pre-processes data received from various sources to change the data into a format used by the computing server 130. For genealogical data, the sample pre-processing engine 215 may receive data from an individual via the user interface 115 of the client device 110. To collect the user data (e.g., genealogical and survey data), the computing server 130 may cause an interactive user interface on the client device 110 to display interface elements in which users can provide genealogical data and survey data. Additional data may be obtained from scans of public records. The data may be manually provided or automatically extracted via, for example, optical character recognition (OCR) performed on census records, town or government records, or any other item of printed or online material. Some records may be obtained by digitalizing written records such as older census records, birth certificates, death certificates, etc.

The sample pre-processing engine 215 may also receive raw data from genetic data extraction service server 125. The genetic data extraction service server 125 may perform laboratory analysis of biological samples of users and generate sequencing results in the form of digital data. The sample pre-processing engine 215 may receive the raw genetic datasets from the genetic data extraction service server 125. The human genome mutation rate is estimated to be $1.1*10^{-8}$ per site per generation. This leads to a variant approximately every 300 base pairs. Most of the mutations that are passed down to descendants are related to single-nucleotide polymorphism (SNP). SNP is a substitution of a single nucleotide that occurs at a specific position in the genome. The sample pre-processing engine 215 may convert the raw base pair sequence into a sequence of genotypes of target SNP sites. Alternatively, the pre-processing of this conversion may be performed by the genetic data extraction service server 125. The sample pre-processing engine 215 identifies autosomal SNPs in an individual's genetic dataset. In one embodiment, the SNPs may be autosomal SNPs. In one embodiment, 700,000 SNPs may be identified in an individual's data and may be stored in genetic data store 205. Alternatively, in one embodiment, a genetic dataset may include at least 10,000 SNP sites. In another embodiment, a genetic dataset may include at least 100,000 SNP sites. In yet another embodiment, a genetic dataset may include at least 300,000 SNP sites. In yet another embodiment, a genetic dataset may include at least 1,000,000 SNP sites. The sample pre-processing engine 215 may also convert the nucleotides into bits. The identified SNPs, in bits or in other suitable formats, may be provided to the phasing engine 220 which phases the individual's diploid genotypes to generate a pair of haplotypes for each user.

The phasing engine 220 phases diploid genetic dataset into a pair of haploid genetic datasets and may perform imputation of SNP values at certain sites whose alleles are missing. An individual's haplotype may refer to a collection of alleles (e.g., a sequence of alleles) that are inherited from a parent.

Phasing may include a process of determining the assignment of alleles (particularly heterozygous alleles) to chromosomes. Owing to sequencing conditions and other constraints, a sequencing result often includes data regarding a pair of alleles at a given SNP locus of a pair of chromosomes but may not be able to distinguish which allele belongs to which specific chromosome. The phasing engine 220 uses a genotype phasing algorithm to assign one allele to a first chromosome and another allele to another chromosome. The genotype phasing algorithm may be developed based on an assumption of linkage disequilibrium (LD), which states that haplotype in the form of a sequence of alleles tends to cluster together. The phasing engine 220 is configured to generate phased sequences that are also commonly observed in many other samples. Put differently, haplotype sequences of different individuals tend to cluster together. A haplotype-cluster model may be generated to determine the probability distribution of a haplotype that includes a sequence of alleles. The haplotype-cluster model may be trained based on labeled data that includes known phased haplotypes from a trio (parents and a child). A trio is used as a training sample because the correct phasing of the child is almost certain by comparing the child's genotypes to the parent's genetic datasets. The haplotype-cluster model may be generated iteratively along with the phasing process with a large number of unphased genotype datasets. The haplotype-cluster model may also be used to impute one or more missing data.

By way of example, the phasing engine 220 may use a directed acyclic graph model such as a hidden Markov model (HMM) to perform phasing of a target genotype dataset. The directed acyclic graph may include multiple levels, each level having multiple nodes representing different possibilities of haplotype clusters. An emission probability of a node, which may represent the probability of having a particular haplotype cluster given an observation of the genotypes may be determined based on the probability distribution of the haplotype-cluster model. A transition probability from one node to another may be initially assigned to a non-zero value and be adjusted as the directed acyclic graph model and the haplotype-cluster model are trained. Various paths are possible in traversing different levels of the directed acyclic graph model. The phasing engine 220 determines a statistically likely path, such as the most probable path or a probable path that is at least more likely than 95% of other possible paths, based on the transition probabilities and the emission probabilities. A suitable dynamic programming algorithm such as the Viterbi algorithm may be used to determine the path. The determined path may represent the phasing result. U.S. patent application Ser. No. 15/519,099, entitled "Haplotype Phasing Models," filed on Oct. 19, 2015, describes one possible embodiment of haplotype phasing.

The IBD estimation engine 225 estimates the amount of shared genetic segments between a pair of individuals based on phased genotype data (e.g., haplotype datasets) that are stored in the genetic data store 205. IBD segments may be segments identified in a pair of individuals that are putatively determined to be inherited from a common ancestor. The IBD estimation engine 225 retrieves a pair of haplotype datasets for each individual. The IBD estimation engine 225 may divide each haplotype dataset sequence into a plurality of windows. Each window may include a fixed number of SNP sites (e.g., about 100 SNP sites). The IBD estimation engine 225 identifies one or more seed windows in which the alleles at all SNP sites in at least one of the phased haplotypes between two individuals are identical. The IBD estimation engine 225 may expand the match from the seed windows to nearby windows until the matched windows reach the end of a chromosome or until a homozygous mismatch is found, which indicates the mismatch is not attributable to potential errors in phasing or in imputation. The IBD estimation engine 225 determines the total length of matched segments, which may also be referred to as IBD segments. The length may be measured in the genetic distance in the unit of centimorgans (cM). A unit of centimorgan may be a genetic length. For example, two genomic positions that are one cM apart may have a 1% chance during each meiosis of experiencing a recombination event between the two positions. The computing server 130 may save data regarding individual pairs who share a length of IBD segments exceeding a predetermined threshold (e.g., 6 cM), in a suitable data store such as in the genealogical data store 200. U.S. patent application Ser. No. 14/029,765, entitled "Identifying Ancestral Relationships Using a Continuous stream of Input," filed on Sep. 17, 2013, and U.S. patent application Ser. No. 15/519,104, entitled "Reducing Error in Predicted Genetic Relationships," filed on Apr. 13, 2017, describe example embodiments of IBD estimation.

Typically, individuals who are closely related share a relatively large number of IBD segments, and the IBD segments tend to have longer lengths (individually or in aggregate across one or more chromosomes). In contrast, individuals who are more distantly related share relatively fewer IBD segments, and these segments tend to be shorter (individually or in aggregate across one or more chromosomes). For example, while close family members often share upwards of 71 cM of IBD (e.g., third cousins), more distantly related individuals may share less than 12 cM of IBD. The extent of relatedness in terms of IBD segments between two individuals may be referred to as IBD affinity. For example, the IBD affinity may be measured in terms of the length of IBD segments shared between two individuals.

Community assignment engine 230 assigns individuals to one or more genetic communities based on the genetic data of the individuals. A genetic community may correspond to an ethnic origin or a group of people descended from a common ancestor. The granularity of genetic community classification may vary depending on embodiments and methods used in assigning communities. For example, in one embodiment, the communities may be African, Asian, European, etc. In another embodiment, the European community may be divided into Irish, German, Swedes, etc. In yet another embodiment, the Irish may be further divided into Irish in Ireland, Irish immigrated to America in 1800, Irish immigrated to America in 1900, etc. The community classification may also depend on whether a population is admixed or unadmixed. For an admixed population, the classification may further be divided based on different ethnic origins in a geographical region.

Community assignment engine 230 may assign individuals to one or more genetic communities based on their genetic datasets using machine learning models trained by unsupervised learning or supervised learning. In an unsupervised approach, the community assignment engine 230 may generate data representing a partially connected undirected graph. In this approach, the community assignment engine 230 represents individuals as nodes. Some nodes are connected by edges whose weights are based on IBD affinity between two individuals represented by the nodes. For example, if the total length of two individuals' shared IBD segments does not exceed a predetermined threshold, the nodes are not connected. The edges connecting two nodes are associated with weights that are measured based on the IBD affinities. The undirected graph may be referred to as an IBD network. The community assignment engine 230 uses clustering techniques such as modularity measurement (e.g., the Louvain method) to classify nodes into different clusters in the IBD network. Each cluster may represent a community. The community assignment engine 230 may also determine sub-clusters, which represent sub-communities. The computing server 130 saves the data representing the IBD network and clusters in the IBD network data store 235. U.S. patent application Ser. No. 15/168,011, entitled "Discovering Population Structure from Patterns of Identity-By-Descent," filed on May 28, 2016, describes one possible embodiment of community detection and assignment.

The community assignment engine 230 may also assign communities using supervised techniques. For example, genetic datasets of known genetic communities (e.g., individuals with confirmed ethnic origins) may be used as training sets that have labels of the genetic communities. Supervised machine learning classifiers, such as logistic regressions, support vector machines, random forest classifiers, and neural networks may be trained using the training set with labels. A trained classifier may distinguish binary or multiple classes. For example, a binary classifier may be trained for each community of interest to determine whether a target individual's genetic dataset belongs or does not belong to the community of interest. A multi-class classifier such as a neural network may also be trained to determine whether the target individual's genetic dataset most likely belongs to one of several possible genetic communities.

Reference panel sample store 240 stores reference panel samples for different genetic communities. A reference panel sample is a genetic data of an individual whose genetic data is the most representative of a genetic community. The genetic data of individuals with the typical alleles of a genetic community may serve as reference panel samples. For example, some alleles of genes may be over-represented (e.g., being highly common) in a genetic community. Some genetic datasets include alleles that are commonly present among members of the community. Reference panel samples may be used to train various machine learning models in classifying whether a target genetic dataset belongs to a community, in determining the ethnic composition of an individual, and in determining the accuracy in any genetic data analysis, such as by computing a posterior probability of a classification result from a classifier.

A reference panel sample may be identified in different ways. In one embodiment, an unsupervised approach in community detection may apply the clustering algorithm recursively for each identified cluster until the sub-clusters contain a number of nodes that is smaller than a threshold (e.g., contains fewer than 1000 nodes). For example, the community assignment engine 230 may construct a full IBD network that includes a set of individuals represented by nodes and generate communities using clustering techniques. The community assignment engine 230 may randomly sample a subset of nodes to generate a sampled IBD network. The community assignment engine 230 may recursively apply clustering techniques to generate communities in the sampled IBD network. The sampling and clustering may be repeated for different randomly generated sampled IBD networks for various runs. Nodes that are consistently assigned to the same genetic community when sampled in various runs may be classified as a reference panel sample. The community assignment engine 230 may measure the consistency in terms of a predetermined threshold. For example, if a node is classified to the same community 95% (or another suitable threshold) of times whenever the node is sampled, the genetic dataset corresponding to the individual represented by the node may be regarded as a reference panel sample. Additionally, or alternatively, the community assignment engine 230 may select N most consistently assigned nodes as a reference panel for the community.

Other ways to generate reference panel samples are also possible. For example, the computing server 130 may collect a set of samples and gradually filter and refine the samples until high-quality reference panel samples are selected. For example, a candidate reference panel sample may be selected from an individual whose recent ancestors are born at a certain birthplace. The computing server 130 may also draw sequence data from the Human Genome Diversity Project (HGDP). Various candidates may be manually screened based on their family trees, relatives' birth location, other quality control. Principal component analysis may be used to creates clusters of genetic data of the candidates. Each cluster may represent an ethnicity. The predictions of the ethnicity of those candidates may be compared to the ethnicity information provided by the candidates to perform further screening.

The ethnicity estimation engine 245 estimates the ethnicity composition of a genetic dataset of a target individual. The genetic datasets used by the ethnicity estimation engine 245 may be genotype datasets or haplotype datasets. For example, the ethnicity estimation engine 245 estimates the ancestral origins (e.g., ethnicity) based on the individual's genotypes or haplotypes at the SNP sites. To take a simple example of three ancestral populations corresponding to African, European and Native American, an admixed user may have nonzero estimated ethnicity proportions for all three ancestral populations, with an estimate such as [0.05, 0.65, 0.30], indicating that the user's genome is 5% attributable to African ancestry, 65% attributable to European ancestry and 30% attributable to Native American ancestry. The ethnicity estimation engine 245 generates the ethnic composition estimate and stores the estimated ethnicities in a data store of computing server 130 with a pointer in association with a particular user.

In one embodiment, the ethnicity estimation engine 245 divides a target genetic dataset into a plurality of windows (e.g., about 1000 windows). Each window includes a small number of SNPs (e.g., 300 SNPs). The ethnicity estimation engine 245 may use a directed acyclic graph model to determine the ethnic composition of the target genetic dataset. The directed acyclic graph may represent a trellis of an inter-window hidden Markov model (HMM). The graph includes a sequence of a plurality of node group. Each node group, representing a window, includes a plurality of nodes. The nodes representing different possibilities of labels of genetic communities (e.g., ethnicities) for the window. A node may be labeled with one or more ethnic labels. For example, a level includes a first node with a first label representing the likelihood that the window of SNP sites belongs to a first ethnicity and a second node with a second label representing the likelihood that the window of SNPs belongs to a second ethnicity. Each level includes multiple nodes so that there are many possible paths to traverses the directed acyclic graph.

The nodes and edges in the directed acyclic graph may be associated with different emission probabilities and transition probabilities. An emission probability associated with a node represents the likelihood that the window belongs to the ethnicity labeling the node given the observation of SNPs in the window. The ethnicity estimation engine 245 determines the emission probabilities by comparing SNPs in the window corresponding to the target genetic dataset to corresponding SNPs in the windows in various reference panel samples of different genetic communities stored in the reference panel sample store 240. The transition probability between two nodes represents the likelihood of transition from one node to another across two levels. The ethnicity estimation engine 245 determines a statistically likely path, such as the most probable path or a probable path that is at least more likely than 95% of other possible paths, based on the transition probabilities and the emission probabilities. A suitable dynamic programming algorithm such as the Viterbi algorithm or the forward-backward algorithm may be used to determine the path. After the path is determined, the ethnicity estimation engine 245 determines the ethnic composition of the target genetic dataset by determining the label compositions of the nodes that are included in the determined path. U.S. patent application Ser. No. 15/209,458, entitled "Local Genetic Ethnicity Determination System," filed on Jul. 13, 2016, describes an example embodiment of ethnicity estimation.

The front-end interface 250 may display various results determined by the computing server 130. The results and data may include the IBD affinity between a user and another individual, the community assignment of the user, the ethnicity estimation of the user, phenotype prediction and evaluation, genealogical data search, family tree and pedigree, relative profile and other information. The front-end interface 250 may be a graphical user interface (GUI) that displays various information and graphical elements. The front-end interface 250 may take different forms. In one case, the front-end interface 250 may be a software application that can be displayed at an electronic device such as a computer or a smartphone. The software application may be developed by the entity controlling the computing server 130 and be downloaded and installed at the client device 110. In another case, the front-end interface 250 may take the form of a webpage interface of the computing server 130 that allows users to access their family tree and genetic analysis results through web browsers. In yet another case, the front-end interface 250 may provide an application program interface (API).

The pedigree identification engine 260 links a target individual to a pedigree of the database by identifying potential pedigrees for the target individual and identifying one or more most probable positions in a potential pedigree. A target individual may wish to identify pedigrees that he or she may potentially belong to. The pedigree identification engine 260 receives a genetic dataset from the target individual as input and outputs potential pedigrees that the target individual may belong to. The pedigree identification engine 260 may further identify one or more probable positions in one of the potential pedigrees based on information associated with matched genetic data between the target individual and DNA test takers in the potential pedigrees. The pedigree identification engine 260 may provide one or more pedigrees for the target individual to select from. For a suggested pedigree, the pedigree identification engine 260 may also provide information of how the target individual is related to other individuals in the pedigree. The pedigree identification engine 260 is discussed in further detail below.

Pedigree Identification

Figure 3:
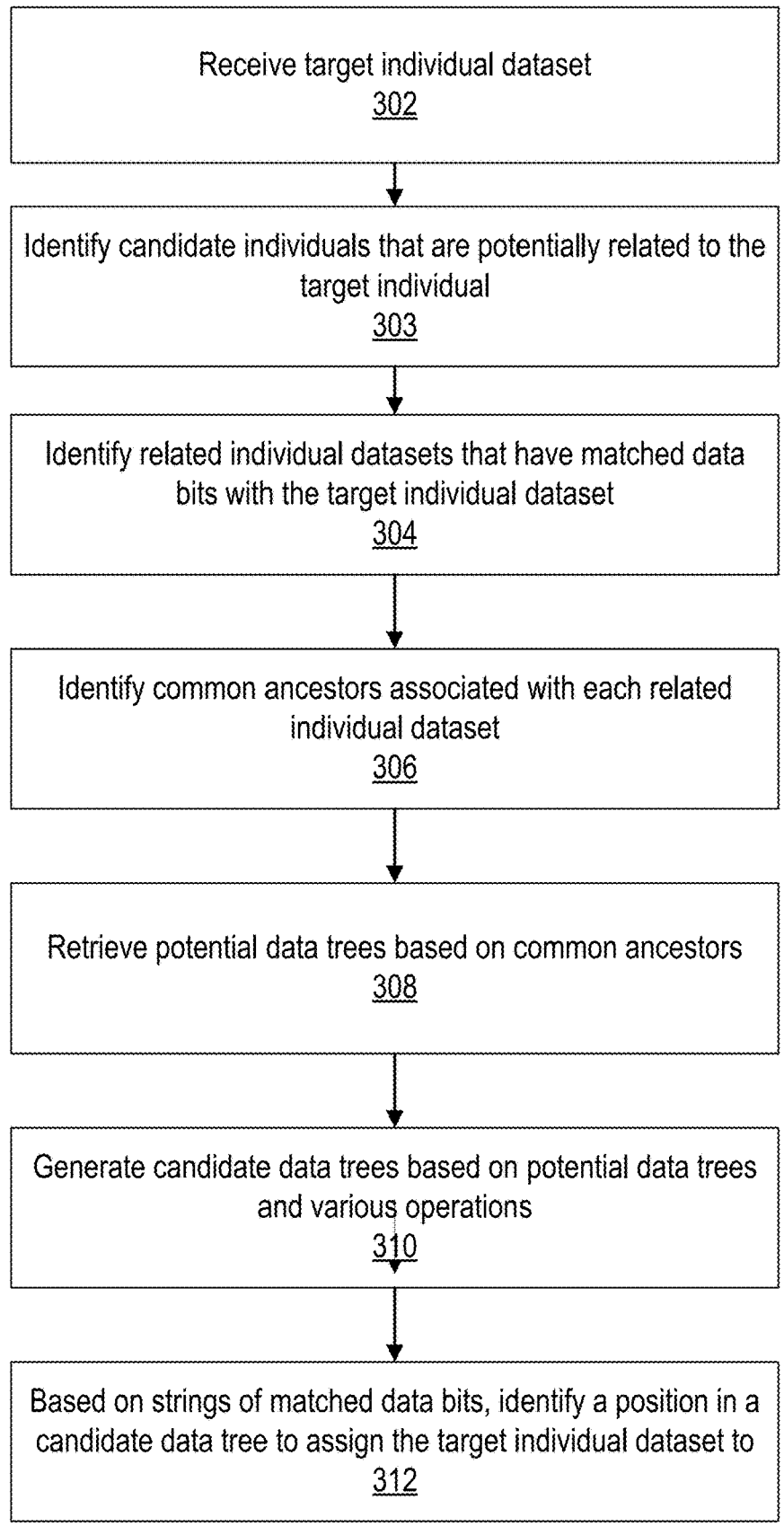
FIG. 3 is a flow chart illustrating an embodiment of a process for linking an individual dataset to a database.

FIG. 3 is a flow chart illustrating an example process that links a target individual to a pedigree, in accordance with an embodiment. Linking the target individual to a pedigree may include determining one or more estimated locations where the target individual should fit at the pedigree based on the genetic and genealogical relationship between the target individual and the individuals in the pedigree. Upon linking the target individual, the computing server 130 may assign metadata to the dataset of the target individual to serve as an indication that the target individual's dataset is linked to the pedigree, which may take the form of a data tree in a database.

The computing server 130 may receive 302 a dataset associated with the target individual. The dataset may contain genetic data such as DNA sequences of the target individual. The genetic data may be sent to various engines of the server 130 such as the sample pre-processing engine 215, phasing engine 220, and IBD estimation engine 235 for data extraction and analysis.

The computing server 130 may identify 303 a plurality of individuals that are potentially related to the target individual. For example, the computing server 130 may identify individuals that have genetic data available in the database as candidate individual. A DNA tester may be a user who has completed a DNA test that extracts the user's DNA data through the genetic data extraction server 125. The extracted genetic data, which may include genotype or haplotype data, is stored in the genetic data store 205. Candidate individual datasets are genetic datasets corresponding to those candidate individuals. The candidate individuals are potentially related to the target individual subject to further analysis.

From the candidate individuals, the computing server 130 may identify 304 one or more related individuals or DNA matches for the target individual based on shared IBD information between the target individual and potential DNA matches. The computing server 130 may identify a related individual dataset from the plurality of candidate individual datasets based on matched data bits such as shared genetic data bits. For example, the computing server 130 may identify a DNA match that has a certain amount of IBD segments shared with the target individual. With IBD estimation engine 235, the computing server 130 may determine the length of IBD segments shared by the target individual and a candidate individual. The computing server 130 may select one or more candidate individuals as potential DNA matches of the individuals based on one or more suitable selection criteria. For example, the criteria may be the shared IBD segments being higher than a threshold, the two individuals being closely related in an IBD community as determined by community assignment engine 230, or other suitable conditions. The DNA matches may be further filtered based on whether the DNA matches have pedigrees available in the database. A DNA match may be referred to as a related individual whose genetic dataset may be referred to as a related individual dataset.

For each identified DNA match, the computing server 130 may identify 306 one or more common ancestors for the target individual and the identified DNA match. The common ancestors may be identified through one or more family trees that are related to the target individual and/or the DNA match. A pedigree or a family tree may be represented as a data tree and a common ancestor may be represented as a parent node, which is a common parent node for both the related individual dataset and the target individual dataset. The common ancestor may be a DNA tester, a non-DNA tester but user of the computing server, or a historical person in a genealogical record.

In some cases, the computing server 130 may identify a potential common ancestor through a "big tree," which may be a large-scale network of individuals whose interrelationships are maintained and discovered by the computing server 130. The computing server 130 may construct a large-scale network by concatenating a large number of family trees of different users. Various users, whether having their genetic data stored in computing server 130 or not, may have constructed one or more family data by using genealogy data store 200 to link individuals, such as DNA testers, other users of computing servers 130 who have not completed a DNA test, or historical individuals whose records are found in one or more genealogical data records. Based on users' permission to share the information, the computing server 130 may generate a large-scale network of individuals that include DNA testers, other users who have not completed DNA tests, and historical individuals. The large-scale network may include a very large number of people (such as many users of the computing server 130 and many other historical individuals who have been included in one or more family trees of users). The computing server 130 may collect a large number of family trees and link the trees together by identifying one or more common individuals in two or more trees.

The computing server 130 may identify one or more potential common ancestors by using one or more family trees, such as using the large-scale network. For example, the computing server 130 may determine that the target individual and the DNA match are in fact connected in the large-scale network. The computing server 130 may identify one or more potential common ancestors who are in the path(s) connecting the target individual and the DNA match. Because one or more potential common ancestors may be identified through the large-scale network, those potential common ancestors may not be individuals who are listed in the target individual's genealogical profile, the DNA match's genealogical profile, or any of the two persons' family trees.

The computing server 130 may provide one or more DNA matches for a user (who is usually the target individual) to select through a user interface. Based on the selection of a DNA match, the computing server 130 may provide one or more suggestions of potential common ancestors to the target individual. The user has the option to select one of the potential common ancestors to further explore. The computing server 130 may receive the user's selection and may start to retrieve connections that form a path between the target individual and the DNA match through the selected potential common ancestor. To complete a full connection, the computing server 130 may first identify a connection who has a linkage that connects the target individual towards the selected potential common ancestor. The computing server 130 may identify a connection who has a linkage that connects the DNA match towards the selected potential common ancestor. After one or more connections are retrieved and established, the above steps may be repeated until the path between the target individual and the DNA match through the common ancestor is completed. Alternatively, or additionally, the computing server 130 may connect the first linkage and the second linkage with the selected potential common ancestor by adding one or more individuals to complete the connection. One example embodiment describing identification of common ancestors is described in U.S. patent application Ser. No. 16/803,219, entitled "Graphical Use Interface Displaying Relatedness Based on Shared DNA," which is incorporated by reference in its entirety for all purposes.

In some cases, the number of identified common ancestors may be enormous and hard to manipulate, the identified common ancestors may be pruned and filtered to the ones that are the most likely to be common ancestors that connect the target individual with the DNA matches. Steps for pruning common ancestors are discussed in detail in FIG. 4. With the identified common ancestors, the computing server 130 may retrieve 308 pedigrees associated with the identified closest common ancestors. For example, the computing server 130 may retrieve data trees that the identified parent nodes belong to. The data trees contain inter-relationships among datasets of the individuals in the data trees. These pedigrees may be referred to as potential pedigrees that the target individual may belong to. The potential pedigrees may be identified through the large-scale network, "big tree," by retrieving all descendants of a closest common ancestor with the closest common ancestor as the root of the pedigree. Along with the potential pedigrees, the computing server 130 also retrieves genetic information of the individuals who are in the potential pedigrees and have genetic information available. With the retrieved potential pedigrees and genetic information for individuals in the potential pedigrees, the computing server 130 may determine a position of the target individual to assign in the potential pedigrees.

To assign the target individual to a position in a potential pedigree, the computing server 130 may perform various operations and generate 310 candidate data trees. In this context, a potential pedigree may refer to an existing pedigree already in the computing server 130 while a candidate data tree may refer to one of the possible trees to place the target individual in an existing pedigree. The candidate data trees may be generated from different operations such as replacing, splitting and extending. The various operations may include replacing, extending or splitting one or more nodes in the potential pedigree. For example, given a pedigree and a target individual, one possible way to fit the target individual in the pedigree is to replace an existing individual that is not a DNA match in the pedigree. A candidate data tree may be generated by replacing an individual in the pedigree with the target individual. The extending operation extends a leaf node in the pedigree by adding the target individual as a decedent of the leaf node. Similarly, the splitting operation may split a parent node in the pedigree by adding the target individual as one of the descendants of the parent node. Each operation may be performed on each applicable node in the pedigree, thereby resulting in a plurality of candidate data trees. Additionally, a candidate data tree may also be generated by assuming the target individual is not related to a common ancestor in the tree, which is discussed in FIG. 5 in accordance with step 509. Details of generating candidate data trees by using these operations is discussed in FIG. 5 and the operations are illustrated in FIGS. 6A-6D.

Since the candidate data trees are generated based on existing pedigrees that include the common ancestors identified from step 306 and the related individuals identified from step 304, each candidate data tree generated from the operations mentioned above contains at least one of the identified DNA matches from step 304. As such, based on the matched DNA information between the target individual and the DNA matches, the computing server 130 may calculate a composite likelihood for each candidate data tree and identify one or more candidate data trees that are likely to be the pedigree to which the target individual belongs. In some embodiment, the most likely candidate data tree is also identified. In turn, the computing server 130 may identify 312 a position in the data tree based on string matched data bits (e.g. IBD segments, data bits in genetic datasets) and number of the matched strings (e.g. IBD spectrum) of the target individual dataset and the datasets of DNA matches in the data tree. The candidate tree also contains the target individual's position information in the pedigree, which indicates the relationship between the target individual and individuals in the pedigree. As a result, an estimated pedigree and a position in the pedigree is determined for the target individual. Detail regarding determination of composite likelihood is discussed in FIG. 5.

To illustrate and summarize the steps performed in FIG. 3 with a non-limiting example, the computing server 130 may identify a number of DNA matches (e.g. 200 DNA matches) for a target individual where the identified DNA matches may be individuals who share top amounts of IBD with the target individual. For each of the 200 DNA matches, a number of potential common ancestors (e.g. 255 common ancestors for each DNA match) may be identified. The total number of identified common ancestor is 200×255, which may be pruned by steps described in FIG. 4. The pruned common ancestors may be referred to as the closest common ancestors and a pedigree associated with each closest common ancestor may be retrieved. For each retrieved pedigree, operations such as replacing, extending and splitting may be performed on each applicable node in the pedigree and a group of candidate trees are generated. Finally, for each candidate data tree, a composite likelihood may be determined based on matched DNA information and a pedigree and a position in the pedigree may be identified for the target individual.

Figure 4:
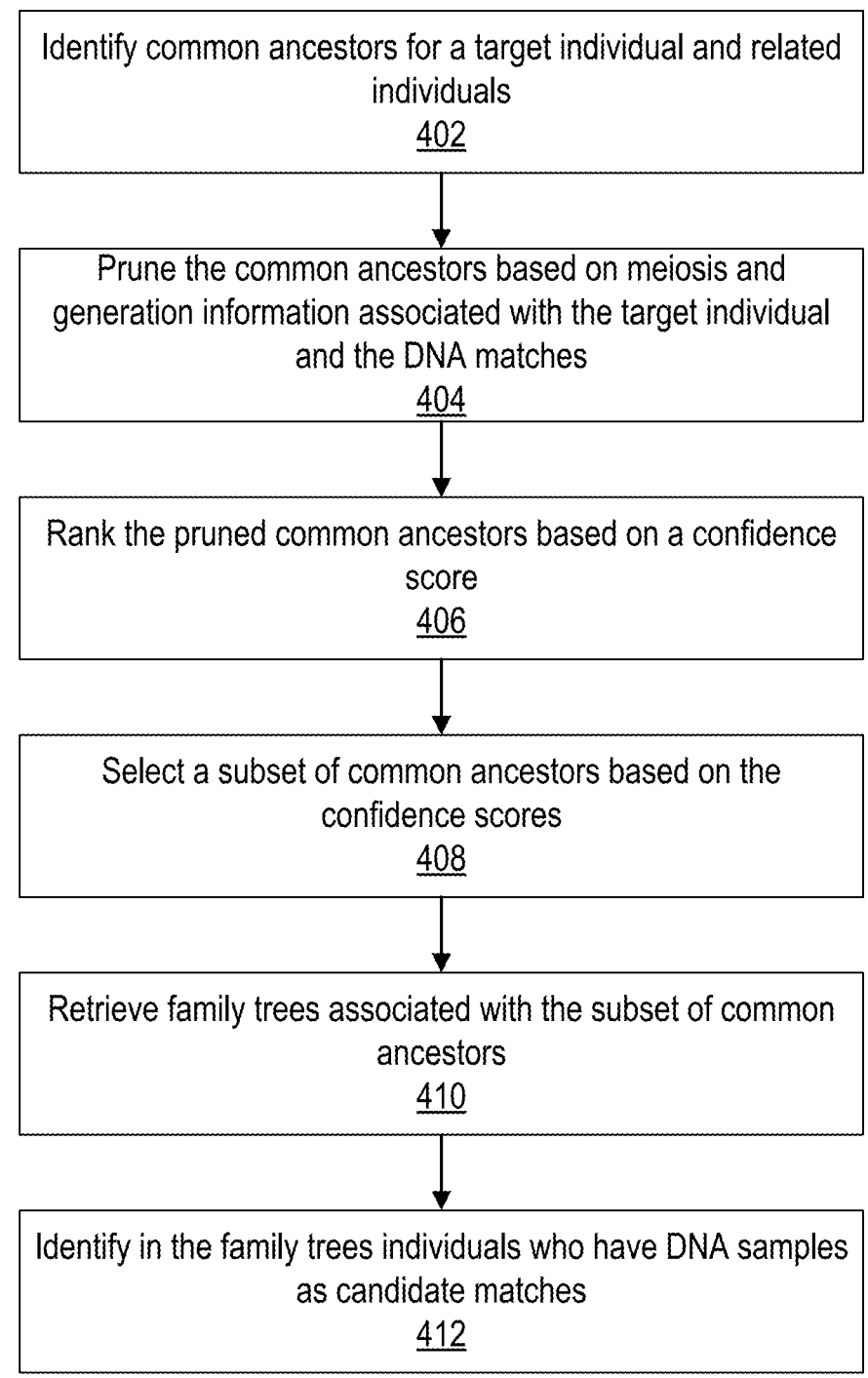
FIG. 4 is a flowchart illustrating an embodiment of a process for identifying potential data trees for a target individual dataset.

FIG. 4 is a flowchart illustrating an embodiment of a process for identifying potential data trees for a target individual dataset. The steps described in FIG. 4 correspond to and expand upon steps 306 and 308 in FIG. 3.

The computing server 130 may identify 402 common ancestors associated with each DNA match. The number of common ancestors could be large. The common ancestors may be represented by candidate parent nodes in one or more data tree. The computing server 130 may prune and rank the large number of common ancestors. The common ancestors may be pruned 404 based on meiosis and generation information associated with the target individual and the DNA matches. Meiosis represents a degree of relatedness of two individuals and is calculated based on the amount of IBD between the two individuals. Through meiosis, a relationship between two individuals may be estimated based on the amount of IBD shared between the pair of individuals. Meiosis may be characterized as the number of reproductive events separating two individuals, and as a result, meiosis is an integer greater than or equal to zero. For example, meiosis between a parent and child is one, because they are separated by one reproductive event. In another example, the meiosis between two full siblings is two, because two meiosis separate two full siblings through the path: sibling 1, parent, sibling 2. For more distant relationship or pairs that include more common ancestors, the meiosis may be calculated in any suitable ways such as based on the detailed framework set forth below in the Section entitled "Calculating M."

A generation value may refer to the number of generations between the common ancestor and the DNA match determined from the pedigree to which both the DNA match and the common ancestor belong. With meiosis information combined with generation value, a portion of the common ancestors may be eliminated. For example, a pair of third cousins may be estimated to have a meiosis of 7 based on IBD, which indicates that they share a most recent common ancestor that is a great-great-grandparent. Determining from pedigrees, third cousins who share a great-great-grandparent in common would have a number of generation value greater than or equal to four. Therefore, if the generation value between the DNA match and the common ancestor is 2, the respective common ancestor may be eliminated. As such, the computing server 130 determines a possible range for a generation value between the related individual and the parent node (e.g. common ancestor) based on a meiosis between the target individual and the related individual (e.g. DNA match). As illustrated in the example above, if the actual generation value (e.g. 2 in the example) is out of the range (e.g. greater than or equal to 4 in the example), the common ancestor is unlikely to be a common ancestor or parent node to both the target individual and the DNA match and the respective common ancestor may be eliminated.

The computing server may also rank 406 the candidate common ancestors (e.g., the remaining common ancestors after pruning) based on a confidence score associated with each candidate common ancestor which is represented by a candidate parent node to the target individual and the DNA match. A confidence score is determined based on meiosis and generation information. In one embodiment, a confidence score may be calculated as $1/(meiosis*generation)$ for meiosis greater than 2. A confidence score may be determined based on other equations or relationships involving meiosis and generation. A confidence score that is closer to one indicates a closer relationship between the target individual and the DNA match and therefore represents a higher level of confidence associated with the common ancestor. For example, for a target individual as a child and a DNA match as a parent, the pair of parent/child has a meiosis of 1 and a generation value of 1. The confidence score for the common ancestor, which is also the parent, is $1/(1*1)=1$, which indicates that the parent is extremely likely to be a true common ancestor. In another example, a meiosis of 2 between a target individual and a DNA match may indicate an immediate family relationship such as siblings, which also leads to a high confidence score. For meiosis values greater than 2, the confidence score is calculated by $1/(meiosis*generation)$. For example, if the meiosis between a target individual and a DNA match is 7 and the generation value between the DNA match and the common ancestor is 4, then the confidence score is calculated as $1/(7*4)=0.0357$.

As such, a confidence score may be calculated for each common ancestor based on meiosis and generation information. The computing server 130 may select a certain number of common ancestors based on the confidence scores. In one embodiment, a certain percentage or a certain number of the highest ranked common ancestors may be selected.

The computing server 130 may retrieve 410 pedigrees associated with the selected closest common ancestors. The pedigrees may be identified through the large-scale network, "big tree," by retrieving all descendants of a closest common ancestor with the closest common ancestor as the root of the pedigree.

The pedigree identification module 260 may scan through the individuals in the retrieved pedigrees and identify 412 individuals who have DNA samples available as candidate matches for the target individual. The pedigree identification module 260 may analyze and retrieve information associated with the candidate matches such as genetic information, IBD, genealogy information or any information available. With the retrieved pedigree information and the candidate matches information, the computing server 130 may determine a position of the target individual in the pedigrees.

Figure 5:
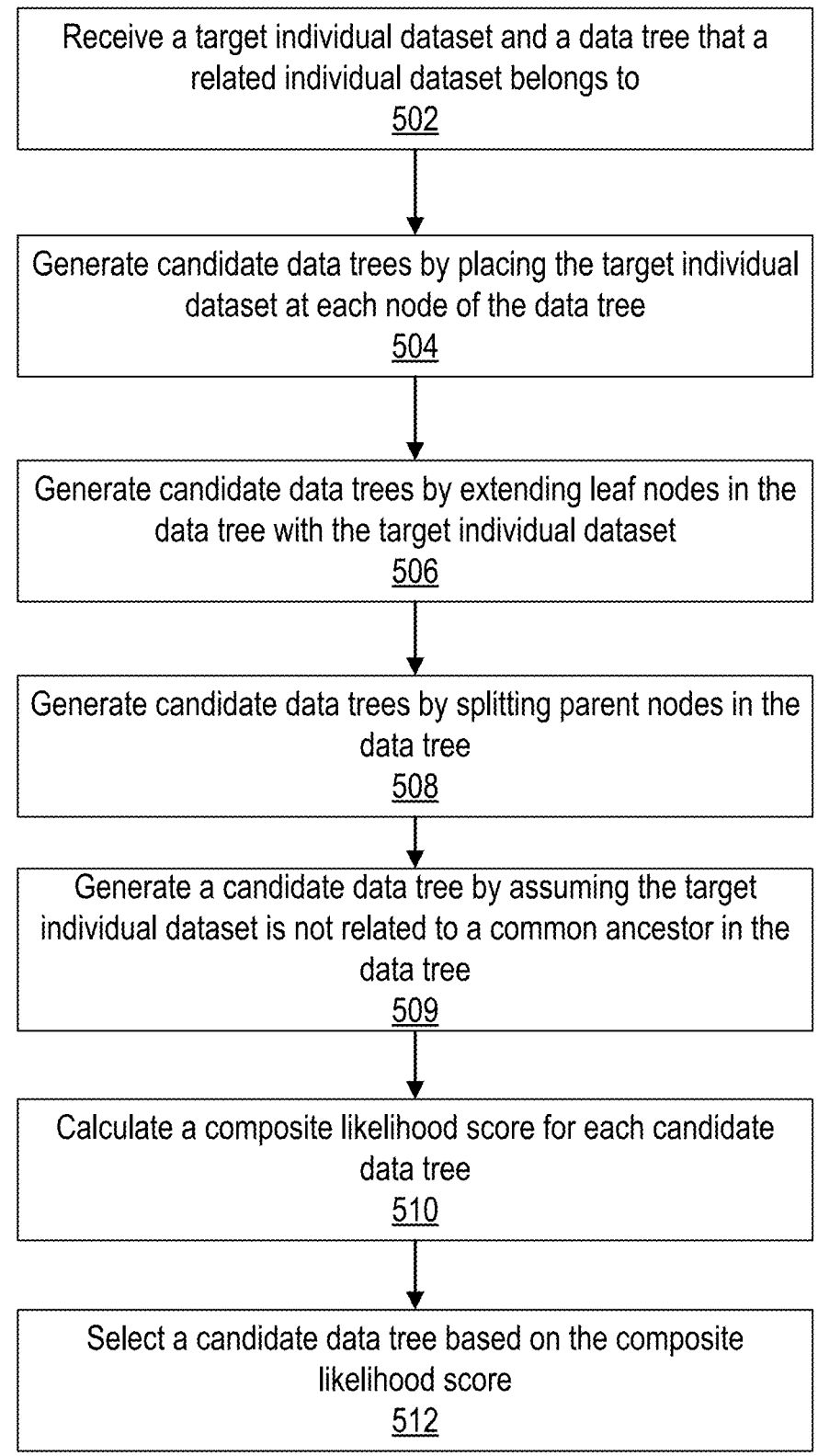
FIG. 5 is a flowchart illustrating an embodiment of a process for assigning a target individual data set to a position in a data tree.

FIG. 5 is a flowchart illustrating an embodiment of a process for assigning a target individual data set to a position in a data tree. The process may be performed repetitively on each pedigree and produce a group of candidate data trees with each candidate data tree representing a possible way indicating how to place the target individual in a pedigree. With information associated with the target individual, a potential pedigree, and candidate matches in the tree, a position of the target individual in the pedigree may be determined.

The determination process starts with receiving 502 data associated with a target individual and a potential pedigree along with candidate matches in the tree. Then various operations such as steps 504-508 are performed on the potential pedigree, which may be referred to as a data tree. The computing server 130 may generate 504 candidate data trees by placing the target individual dataset at each node of the data tree, generate 506 candidate data trees by extending leaf nodes in the data tree with the target individual dataset, generate 508 candidate data trees by splitting parent nodes in the data tree, and generate 509 a candidate data tree by assuming that the target individual is not related to a common ancestor in the potential pedigree. A candidate data tree with a candidate position to place the target individual may be generated through one or more of the following operations. For example, the computing server 130 may assign the target individual to an existing node in the data tree as the candidate position with the target individual replacing the existing node. This operation is further discussed in FIG. 6B. The computing server 130 may add a child node that descends from a leaf node in the data tree as the candidate position for the target individual dataset. This operation is further discussed in FIG. 6C. The computing server 130 may also add a child node that descends from an inner node in the data tree, with the child node in a new branch descending from the inner node and the child node is the candidate position for the target individual dataset. This operation is further discussed in FIG. 6D. Based on the generated candidate data trees, the computing server 130 may calculate 510 a composite likelihood score for each candidate data tree and select 512 a candidate data tree as an estimated pedigree for the target individual based on the composite likelihood score. Each operation 504-508 is illustrated in detail in accordance to FIGS. 6A-6D, which are discussed in further detail.

Figure 6A:
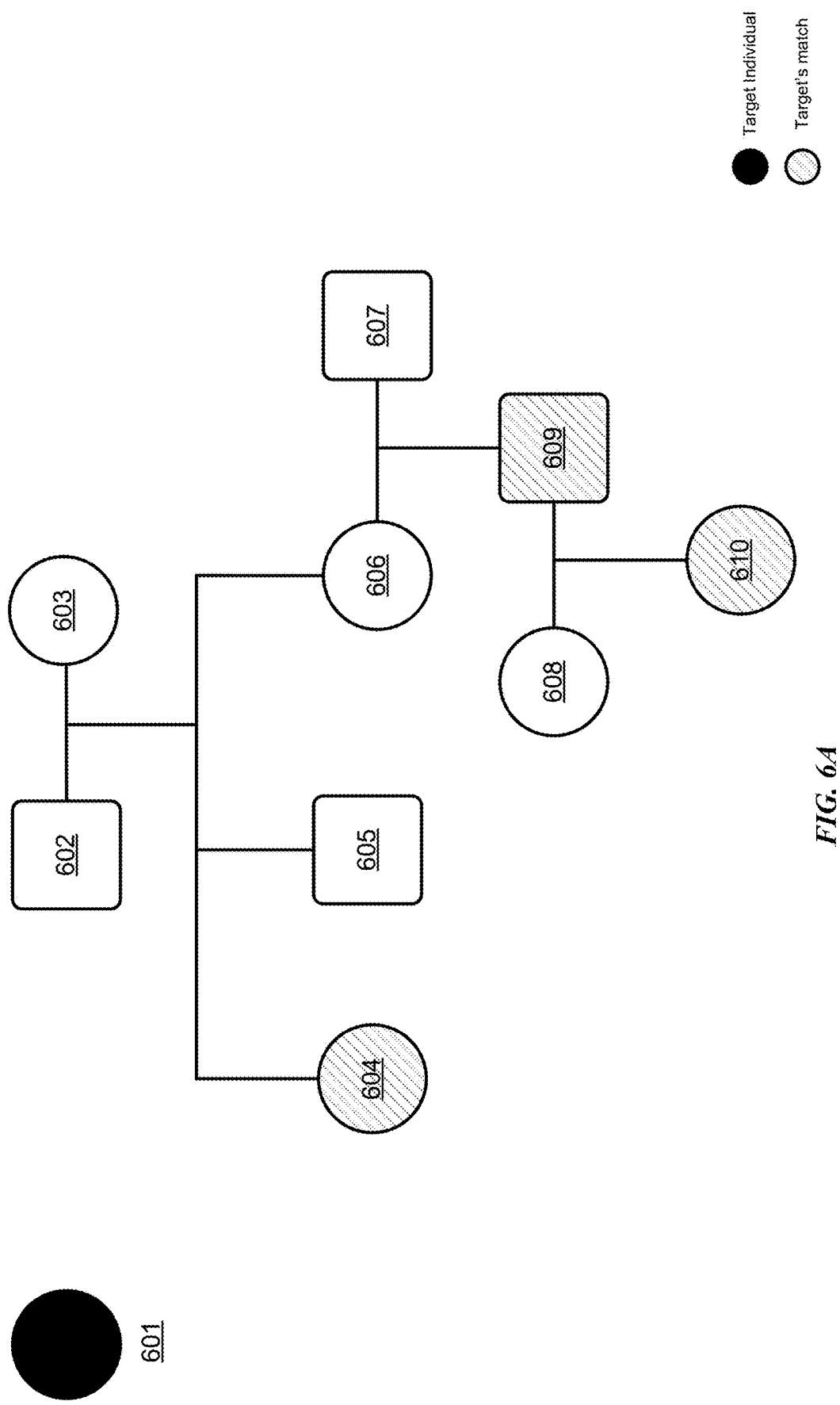
FIGS. 6A-6D illustrate various operations for positioning a target individual dataset in a data tree, in accordance with one embodiment.

FIGS. 6A-6D illustrate various operations for identifying a position for a target individual in a data tree, in accordance with one embodiment. FIG. 6A illustrates a pedigree and a target individual 601 to be placed in the pedigree. In the pedigree, individuals 604, 609 and 610 are candidate matches of the target individual 601.

Figure 6B:
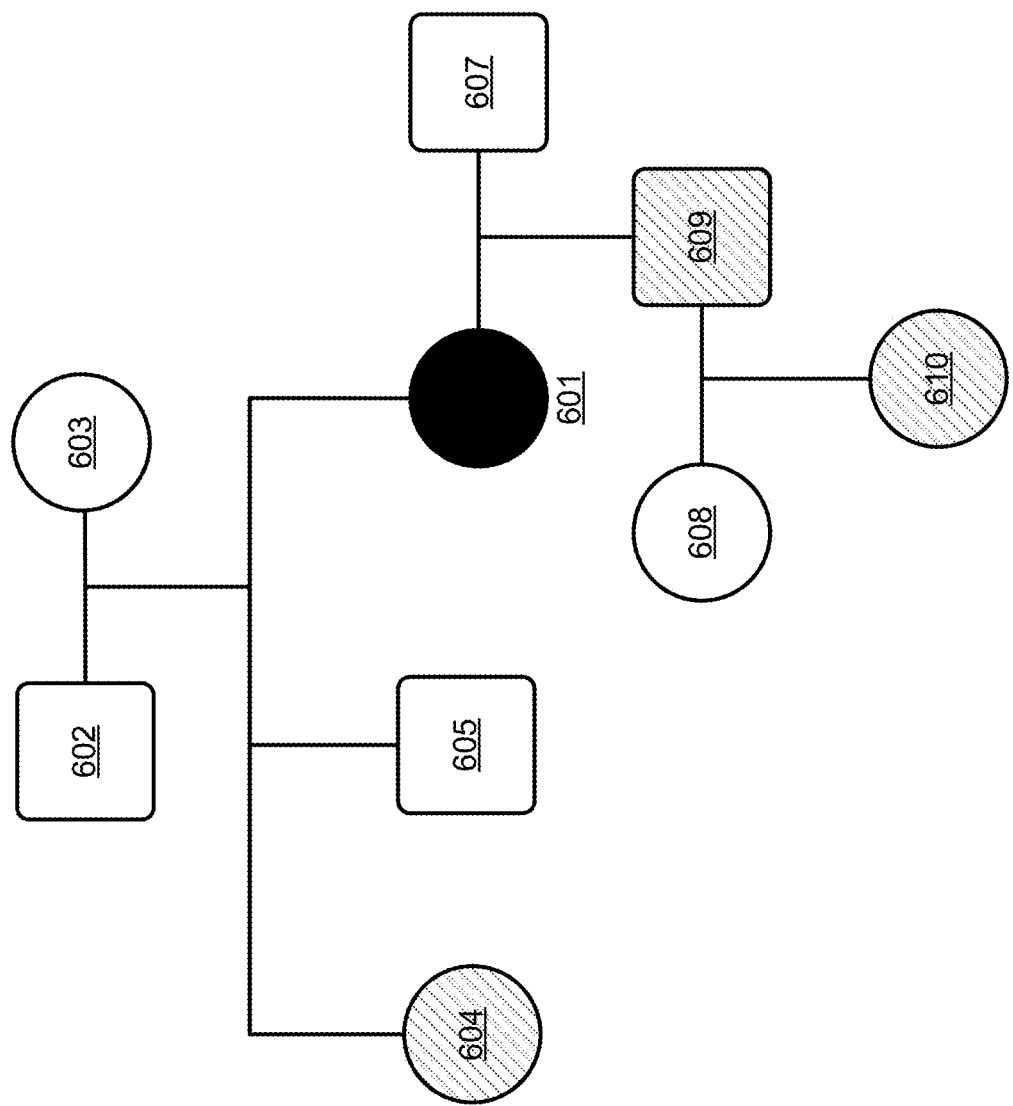

FIG. 6B illustrates an operation that replaces an existing individual in the pedigree that is not the target individual's candidate match. This operation may be an example of operations performed in step 504 in FIG. 5. For example, as illustrated in FIG. 6B, the target individual 601 replaces the position of individual 606 who was originally in the pedigree illustrated in FIG. 6A. The replacing operation may be conducted on each node in the pedigree that is not a candidate match to the target individual 601. In other words, replacing operation on each node may result in a candidate pedigree. For example, the pedigree illustrated in FIG. 6B is one of many possible candidate pedigrees due to replacing operation. Another pedigree may be produced by replacing individual 608 with the target individual 601.

Figure 6C:
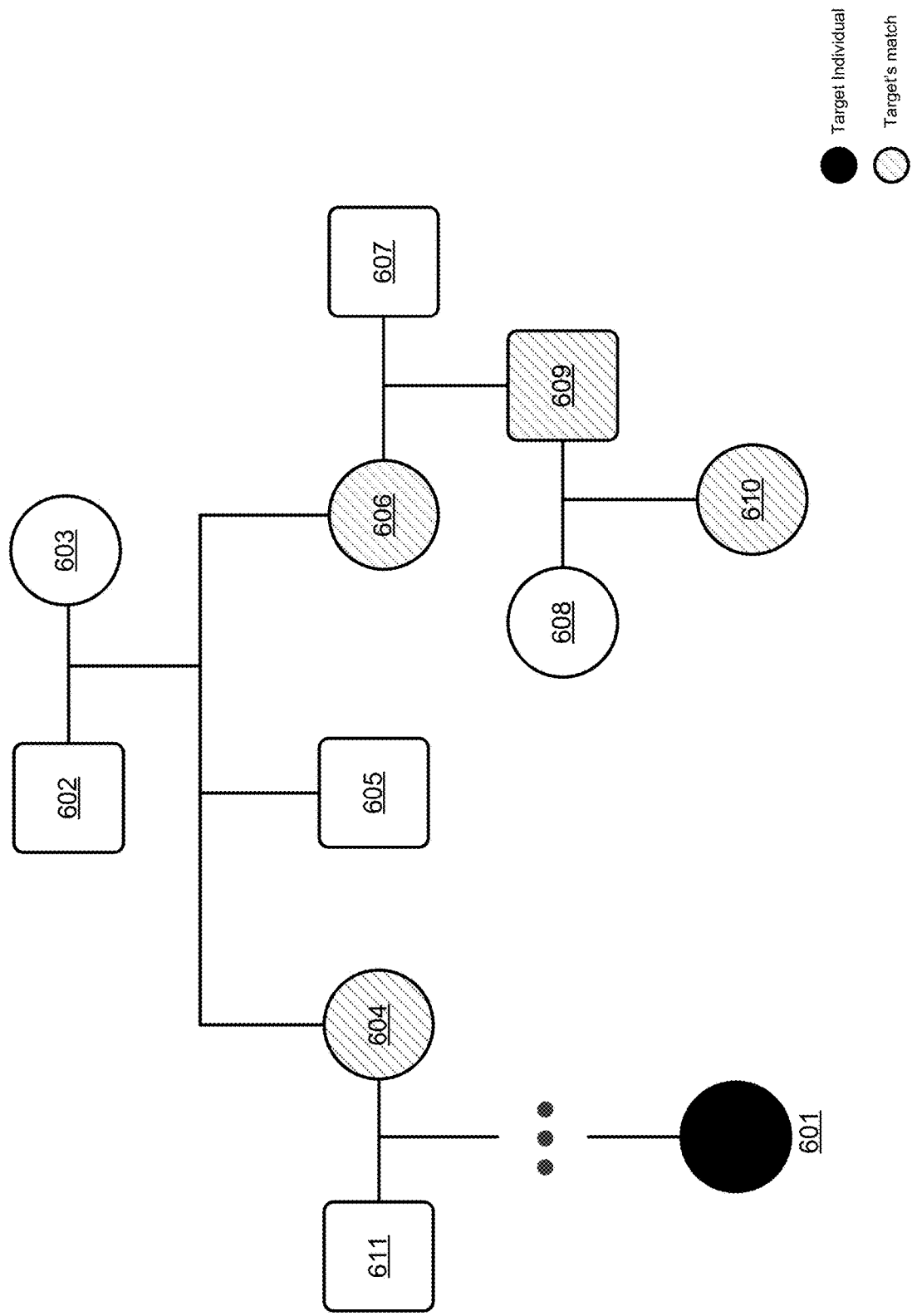

FIG. 6C illustrates an operation that extends a leaf node of the pedigree with the target individual 601, which corresponds to step 506 in FIG. 5. As illustrated in FIG. 6C, the target individual 601 may be a descendant of individual 604. The target individual 601 may be a descendant one generation away from individual 604 or may be any number of generations away. Each different possible way to place the target individual in the pedigree may produce a candidate tree. For example, the target individual may be places one generation apart from individual 604 and results in a first candidate pedigree. The target individual may be two generations apart from individual 604 and results in a second candidate pedigree. In another embodiment, the target individual 601 may be descendant of individual 610 and therefore additional candidate pedigrees may be further generated.

Figure 6D:
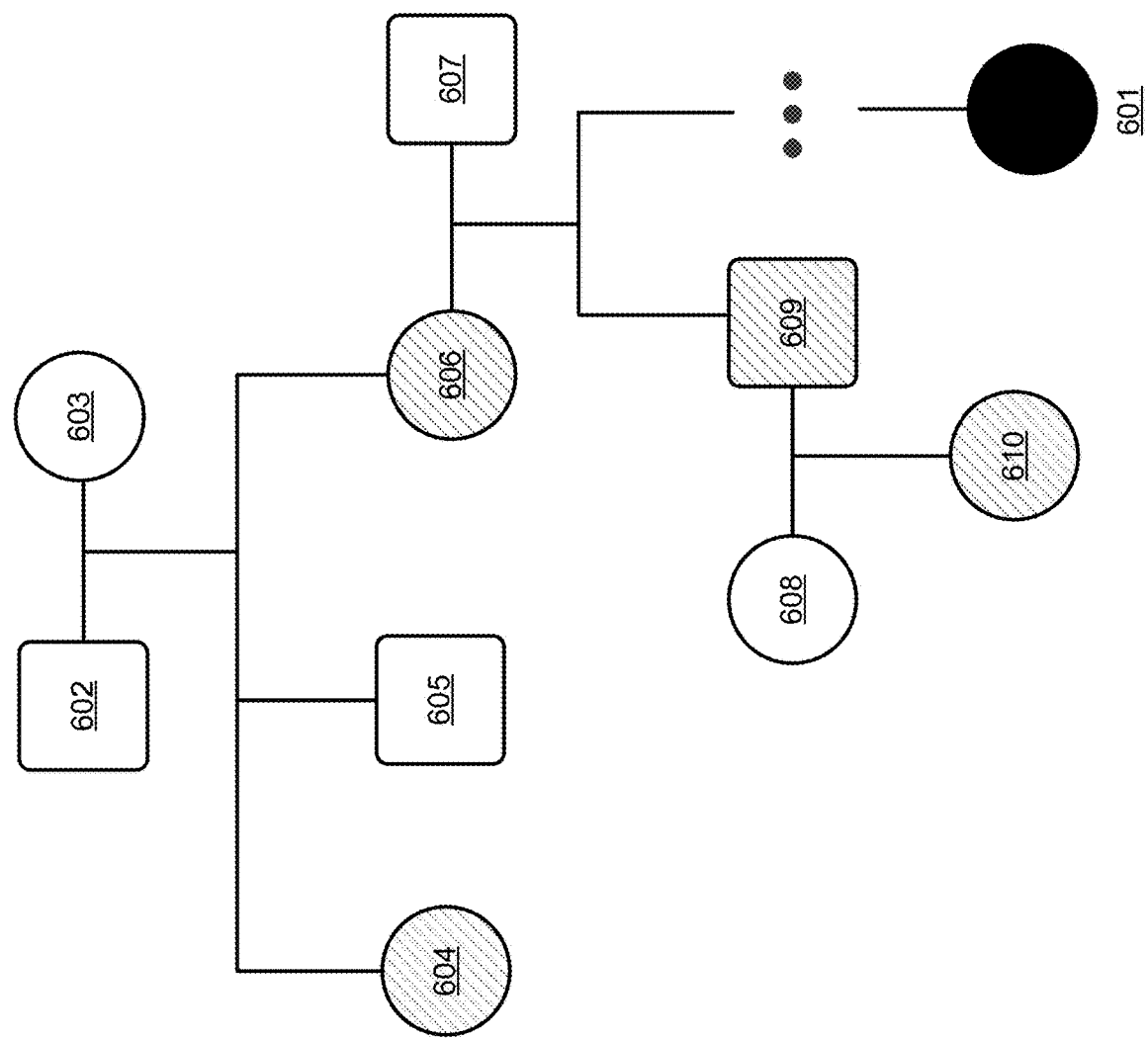

FIG. 6D illustrates an operation that splits a parent node of the pedigree by adding the target individual as a descendant of the parent node, which corresponds to step 508 in FIG. 5. As illustrated in FIG. 6D, individuals 606 and 607 have a descendant 609 as illustrated in the original pedigree in FIG. 6A. The target individual may be another descendant of individuals 606 and 607 in a branch that is parallel to the existing branch that individual 609 belongs to. For example, in FIG. 6D, target individual 601 is placed in the branch that is parallel to individual 609. The target individual may be a descendant that is a number of generations away from an immediate child of individuals 606 and 607 or the target individual 601 may be an immediate child of individuals 606 and 607 (i.e. a sibling of individual 609). Similar to the extending operation, each possible position of target individual 601 may generate a candidate pedigree. For example, if the target individual 601 is one generation away from individuals 606 and 607, a candidate pedigree may be generated. If the target individual is two generations apart from the individuals 606 and 607, another candidate pedigree may be generated. In another possible situation where the target individual 601 is a descendant of individuals 602 and 603, additional possible candidate pedigrees may be generated.

For operations illustrated in FIGS. 6B-6D, optimization may be performed to eliminate positions that are unlikely to assign the target individual to. In one embodiment, optimization may be performed based on metadata associated with the target individual and individuals in the pedigree. Some examples of metadata include but not limited to sex, age, date of birth, date of death or any demographic information. For example, for a replacing operation illustrated in FIG. 6A, if the target individual 601 is a female, then it is unlikely for the target individual to be placed at nodes that are known to be males such as nodes 602, 605, 607 and 608. To illustrate with another example, for an extending operation illustrated in FIG. 6C, the target individual is unlikely to be a descendant of an individual who was born after the target individual. As a result, through optimization based on metadata, a number of potential candidate trees may be eliminated and therefore computational complexity is reduced.

Referring back to FIG. 5, a candidate data tree may also be generated 509 by assuming that the target individual dataset is not related to a common ancestor in the pedigree. If no recent common ancestor information is known, a probability may be determined by integrating over all possible generations at which the two individuals could share a common ancestor.

Continuing with FIG. 5, through various operations such as steps 504-509, candidate trees are generated where each candidate tree represents a possible way to place the target individual in potential pedigrees. For each candidate tree, a composite likelihood score may be calculated 510 based on genetic data and genealogical data associated with the target individual and candidate matches in the candidate tree. Calculation with regard to composite likelihood is discussed in further detail below.

In one embodiment, the likelihood of the relationship between two individuals i and j is calculated based on observed IBD $L_{ij}$ such as length or number of segments of IBD between individuals i and j. The relationship between individuals i and j may be referred to as $g=(g_i, g_j)$. Suppose the pedigree includes M candidate matches, the full likelihood of the IBD sharing may be approximated to be a product of pairwise sharing between the target individual and all other candidates in the pedigree, that is, M pairs of individuals in the network. Therefore, it is necessary to obtain a way of calculating the likelihood of the relationship $g_i, g_j$ between two individuals i, j for observed IBD $L_{ij}$. For ease of notation, the likelihood is expressed as $L(g)=P(L_{ij}|g)$, which may be used as a building block for the composite likelihood.

The first step is to model the length of an IBD segment shared by two related individuals given that the two individuals find a most recent common ancestor (MRCA) at g generations in the past. For a pair of individuals i and j, assume that they do not have more than a single individual or couple that is a recent common ancestor (CA) between (i.e. no inbreeding). Suppose that these individuals find a common ancestor at $g_i$, $g_j$ generations back from their own generation, respectively. With the exception of full siblings (with two IBD sharing segments which violates assumptions), at a given site in the genome, the density of IBD length l (in centimorgans) is given by:

$$p(l \mid g_i, g_j) = \begin{cases} 2^{-g_i-g_j+1+\delta(i,j)}\left(\dfrac{g_i + g_j}{100}\right)^2 l e^{-\frac{g_i+g_j}{100}l}, & \text{if } l > 0 \\ 1 - 2^{-g_i-g_j+1+\delta(i,j)}, & \text{if } l = 0 \end{cases}$$

where, $$\delta(i, j) = \begin{cases} 0, & \text{if } CA(i, j) \text{ is an individual} \\ 1, & \text{if } CA(i, j) \text{ is a couple} \end{cases}$$

Therefore, $\delta(i,j)=0$ is equivalent to one of the two cases: 1) i and j are half-relatives, or 2) i is an ancestor of j or vise-versa. For example, if i is the parent of j, then $\delta(i,j)=0$.

Figure 7A:
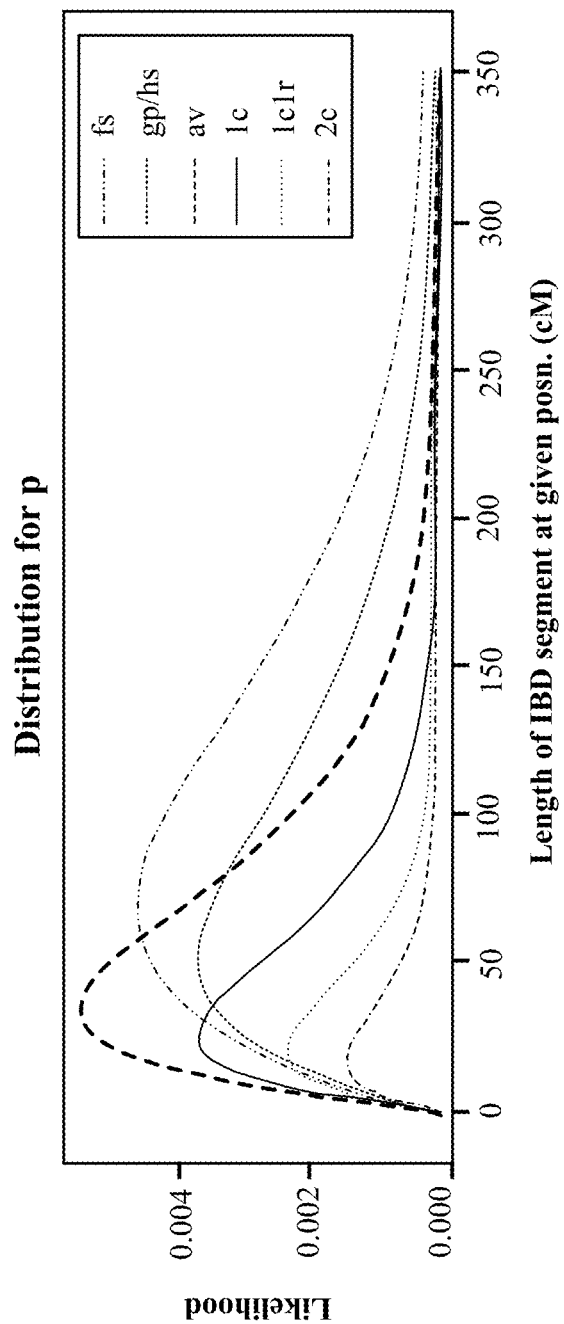
FIGS. 7A-7C illustrate various distributions related to calculation of a composite likelihood.
Figure 7B:
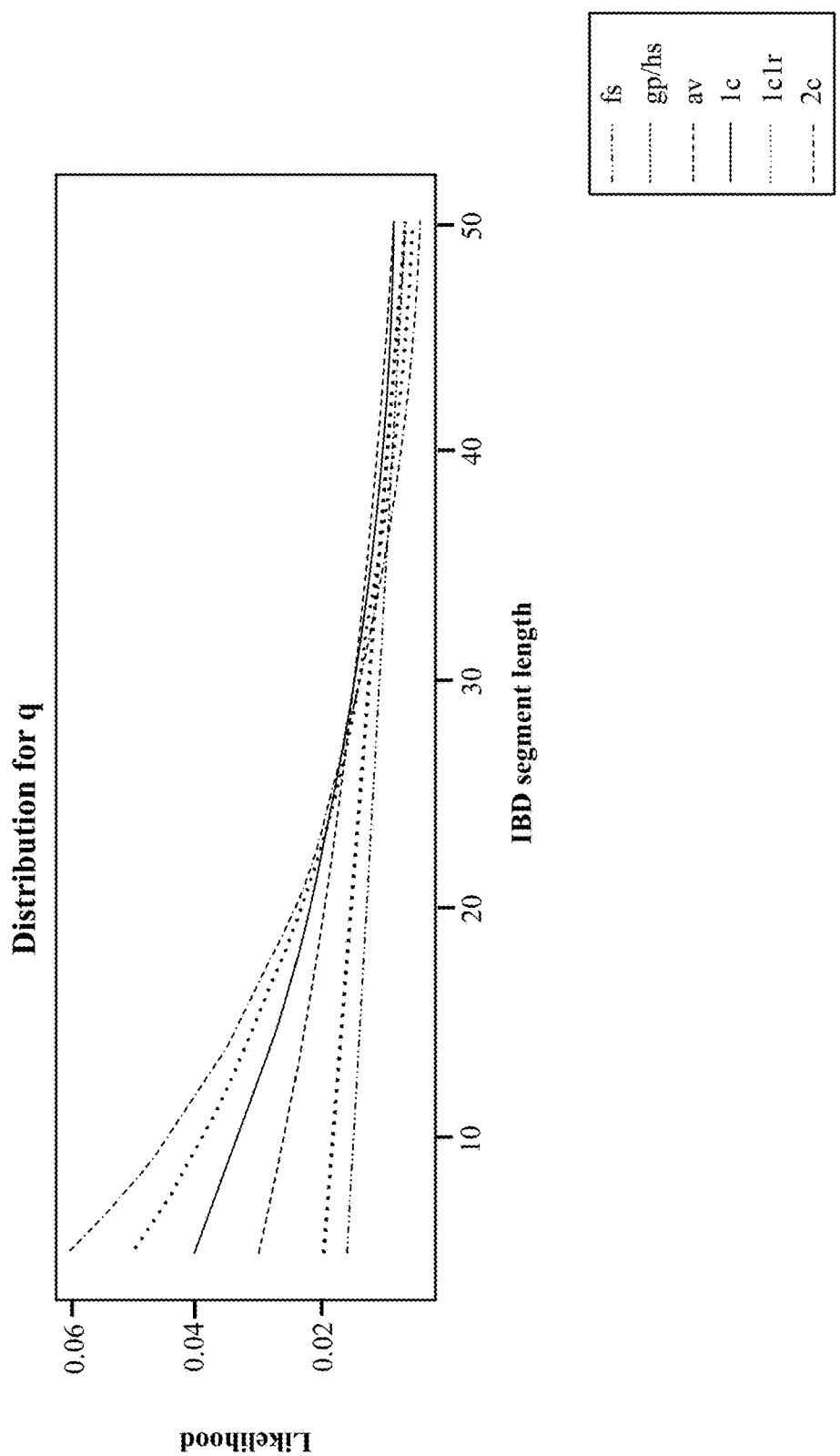
Figure 7C:
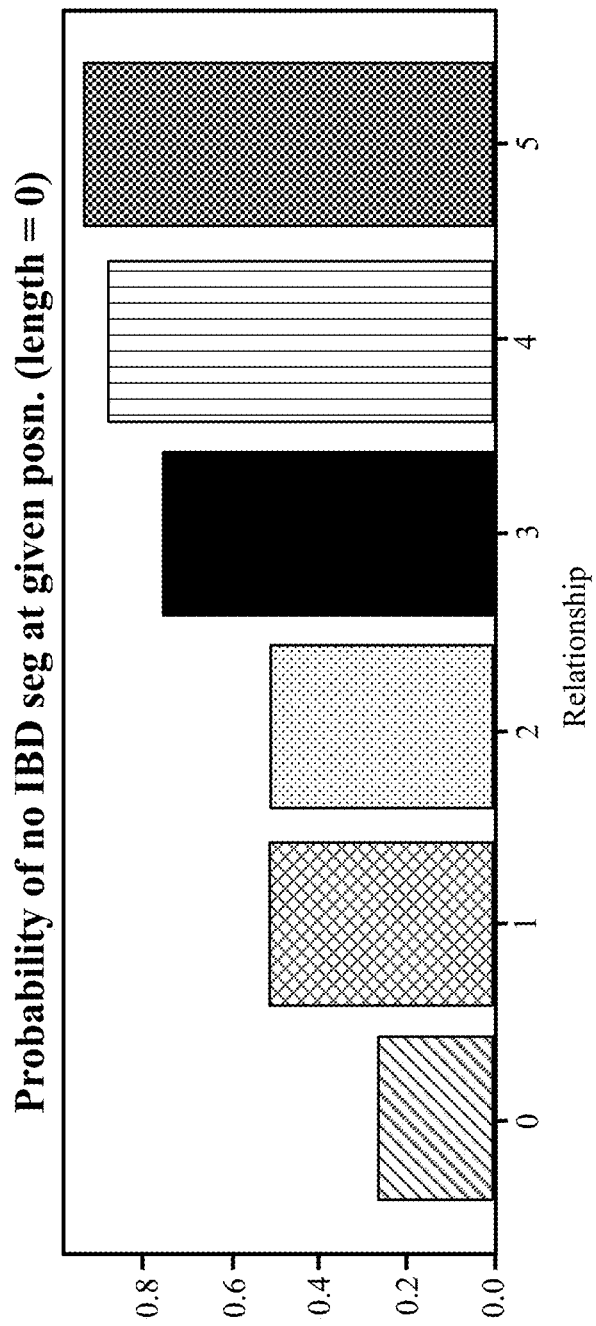

Note that the segment length is conditional on the length being nonzero (i.e. $p(l|l>0, g_i, g_j)$) and has an Erlang-2 distribution. That is, it takes the distribution of the sum of two exponential random variables, each corresponding to the closest recombination breakpoint to the site of interest that has occurred throughout all meiosis between i and j. Specifically, the distribution is equivalent to the distribution of $X_1+X_2$, where $X_1$ and $X_2$ are independent identical distribution (iid) of Exp $$\left(\frac{g_i + g_j}{100}\right),$$

which may be considered as the distribution of the sum of the minimums of two iid vectors of iid Exp(100) variables with one vector of length $g_i$ and the other vector of length $g_j$. Intuitively, the greater the value of g, the more likely the IBD is split into a smaller piece. The distributions of p and q for different relationships are illustrated in FIGS. 7A-7C. FIG. 7A illustrates p, which is the probability density function of segment length at a given position in the genome. FIG. 7B illustrates 1, which is the probability density function of normalized segment length. FIG. 7C illustrates probability of two individuals with no IBD sharing. The illustrated relationships are full sibling (fs), avuncular (av), half sibling (hs), grandparent (gp), kth-cousin (e.g. 1c, 2c) and uth-removed (e.g. 1r).

The second step is to model the spectrum of IBD segments shared by two related individuals. For some observed spectrum of n IBD segments $L=(L_1, L_2, \ldots, L_n)$ shared between i and j, it is assumed that the likelihood for $g=(g_i, g_j)$ is:

$$L(g) = \begin{cases} P(N = n \mid g) \prod_{k=1}^{n} q(l_k \mid g), & \text{if } n > 0 \\ P(N = 0 \mid g), & \text{if } n = 0 \end{cases}$$

It is presumed that given the number of IBD segments, the lengths are conditionally independent of one another and are identically distributed.

Note that the distribution q in the product is a different distribution than the distribution p discussed above. The distribution q may be perceived as the length-normalized distribution of segments, that is, conditioning on any arbitrary N=n, q is the distribution of how frequent a single segment of length l is among those n segments of varying length. The distribution of q is derived as:

$$q(l \mid g) = \frac{p(l \mid g)}{l} \bigg/ \int_0^{+\infty} \frac{p(l \mid g)}{l} dl = \frac{g_i + g_j}{100} e^{-\frac{g_i+g_j}{100}l}$$

As a result from the modeling, the number of segments and the total IBD length are sufficient to infer g, that is:

$$L(g) = P(N = n \mid g) \prod_{k=1}^{n} q(l_k \mid g) = P(N = n \mid g)\left(\frac{g_i + g_j}{100}\right)^n e^{-\frac{g_i+g_j}{100}\Sigma_k l_k}$$

This proves that for most pairwise relationships, the number and the total length of the IBD segments are sufficient to infer the underlying relationship g.

In practice, it is useful to just examine IBD segments that are thresholded below by a certain u>0. In such case, the distribution of q is derived as:

$$q_u(l\mid g) = \frac{p(l\mid g)}{l} \bigg/ \int_u^{+\infty} \frac{p(l\mid g)}{l} dl$$

Figure 8A:
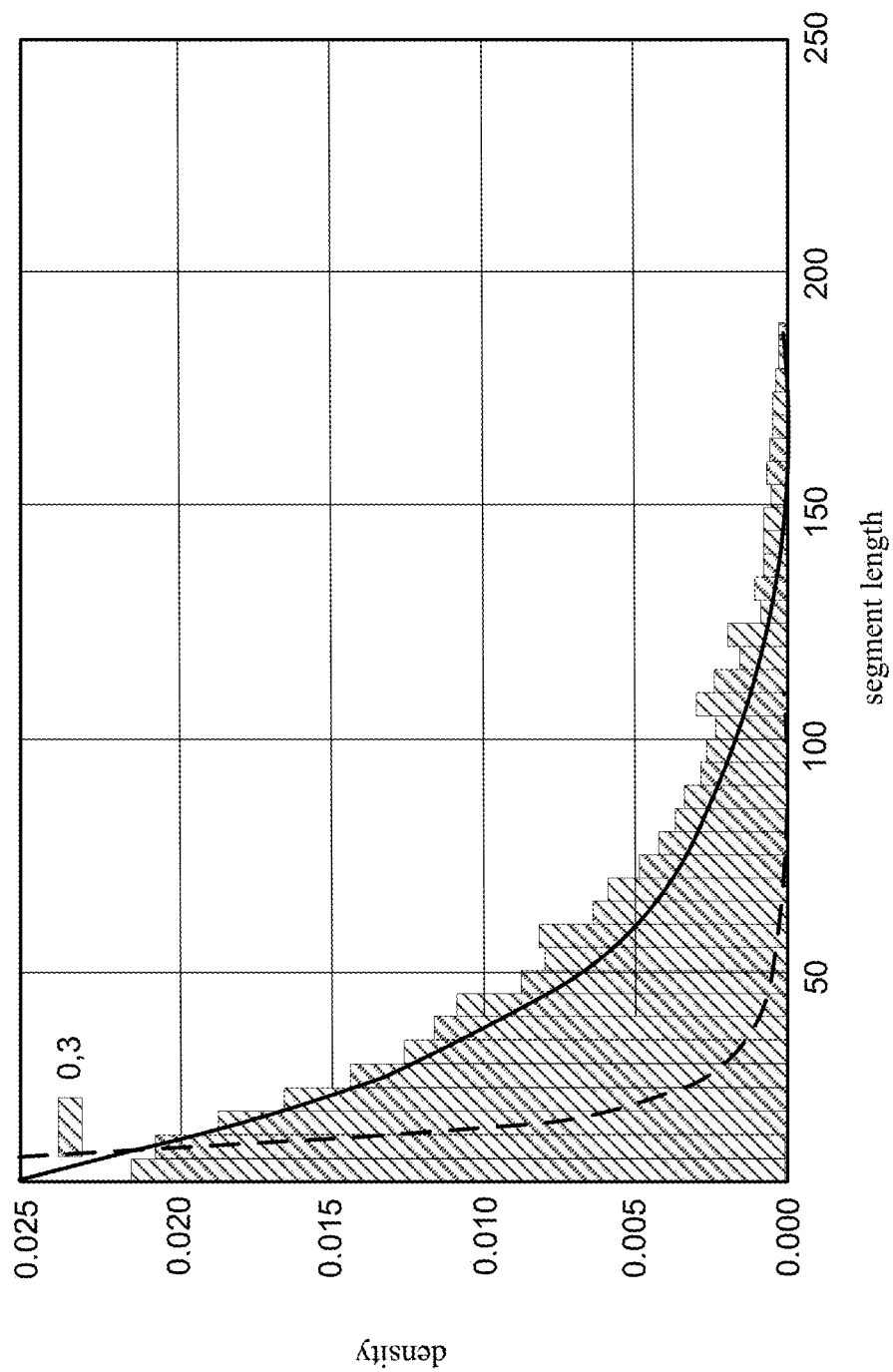
FIG. 8A-C are histograms that illustrate empirical and modeled distributions for segment length.
Figure 8B:
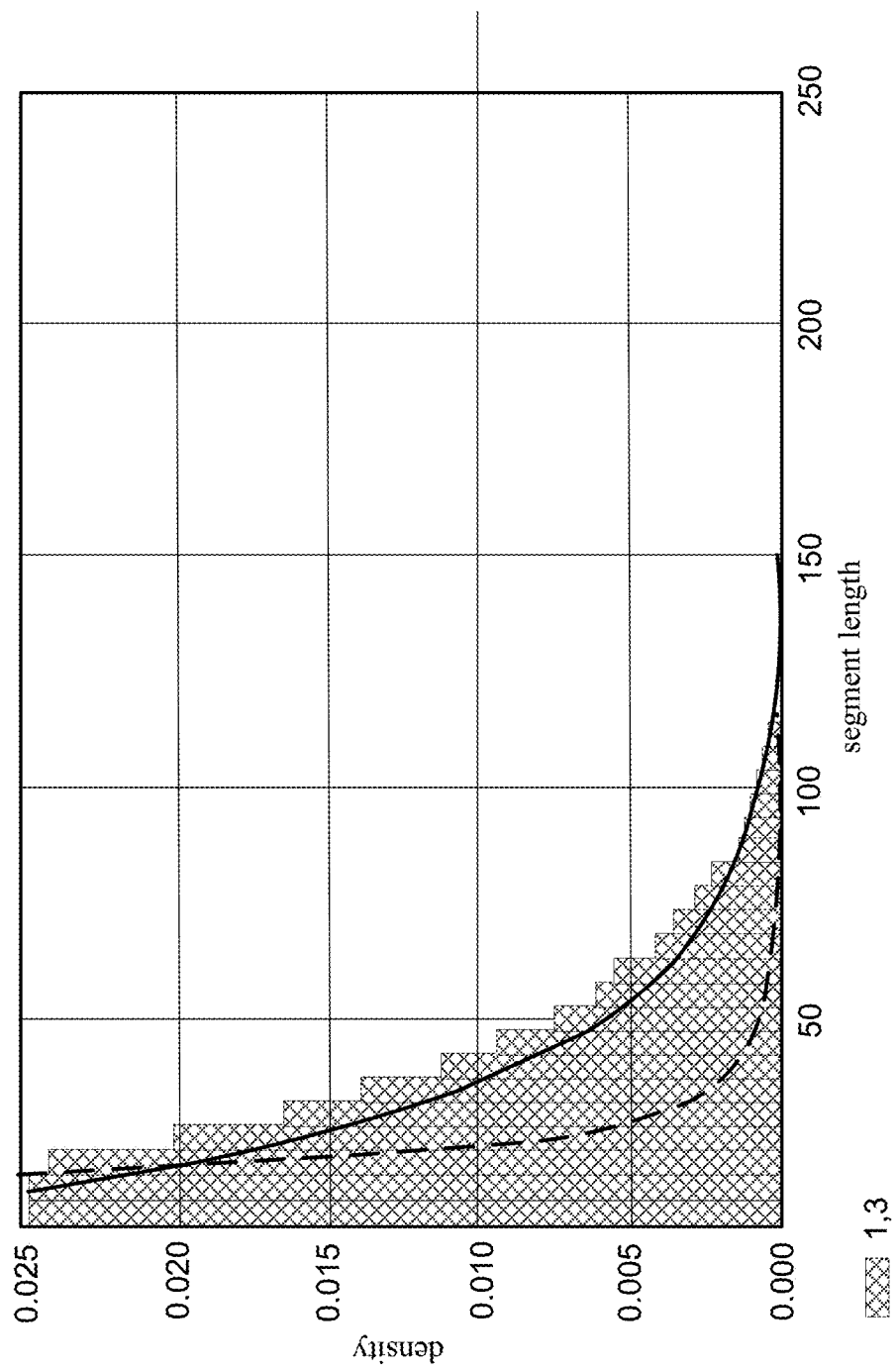
Figure 8C:
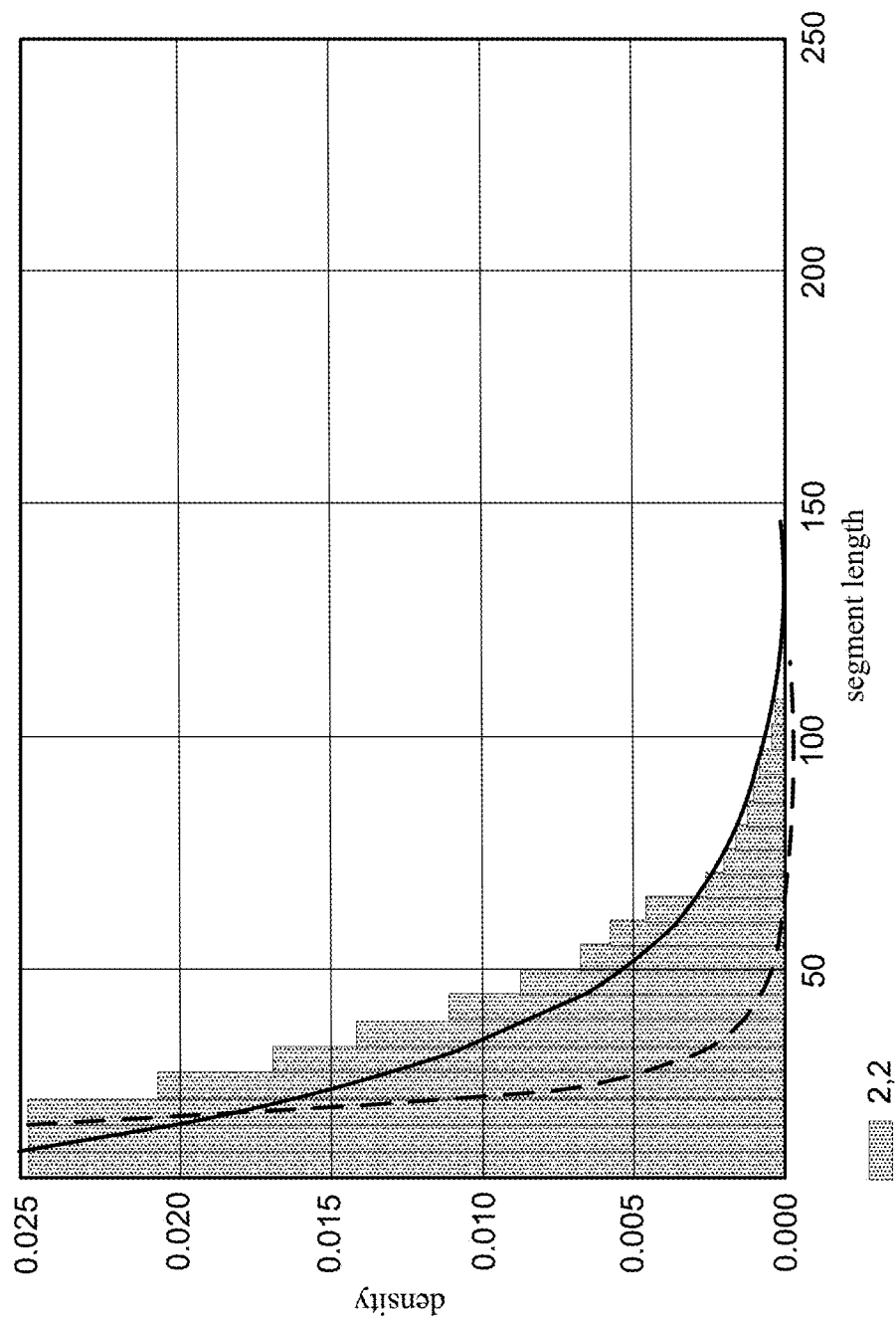

For l>u, the distribution of $q_u$ is proportional to the original q. For example, a threshold u=5 is used in the analysis illustrated in FIGS. 8A-C. FIG. 8A illustrates the empirical distribution of IBD segments for great grandparent (i.e. g=(0, 3)), FIG. 8B illustrates the empirical distribution of IBD segments for grand aunt or grand uncle (i.e. g=(1, 3)), and FIG. 8C illustrates the empirical distribution of IBD segments for 1st cousins (i.e. g=(2, 2)). The solid line in each of the FIGS. 8A-C are the model fit for the respective distribution and the dotted line is the expected segment length distribution for two unrelated individuals.

Figure 9A:
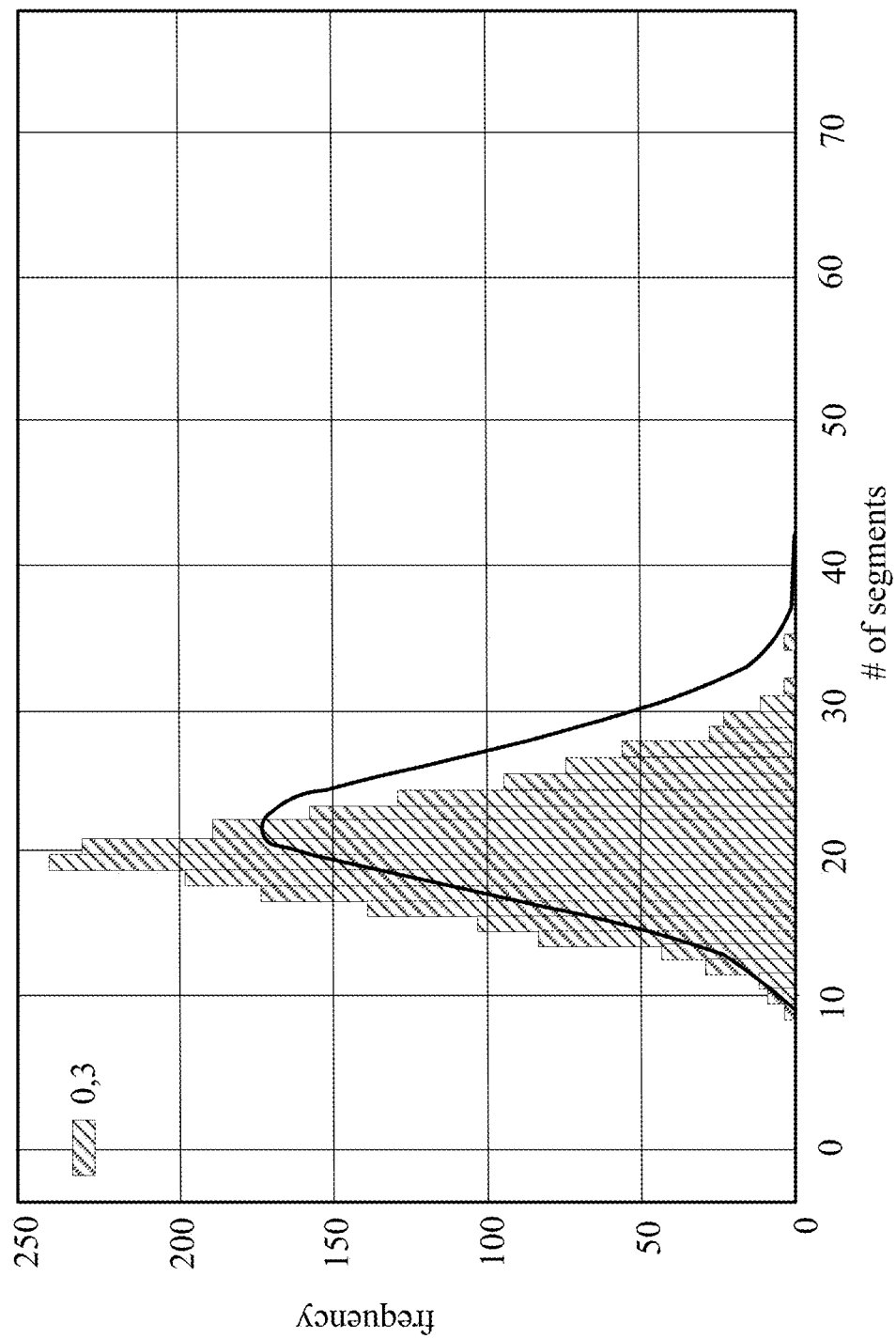
FIG. 9A-C are histograms that illustrate empirical and modeled distributions for the number of IBD segments.
Figure 9B:
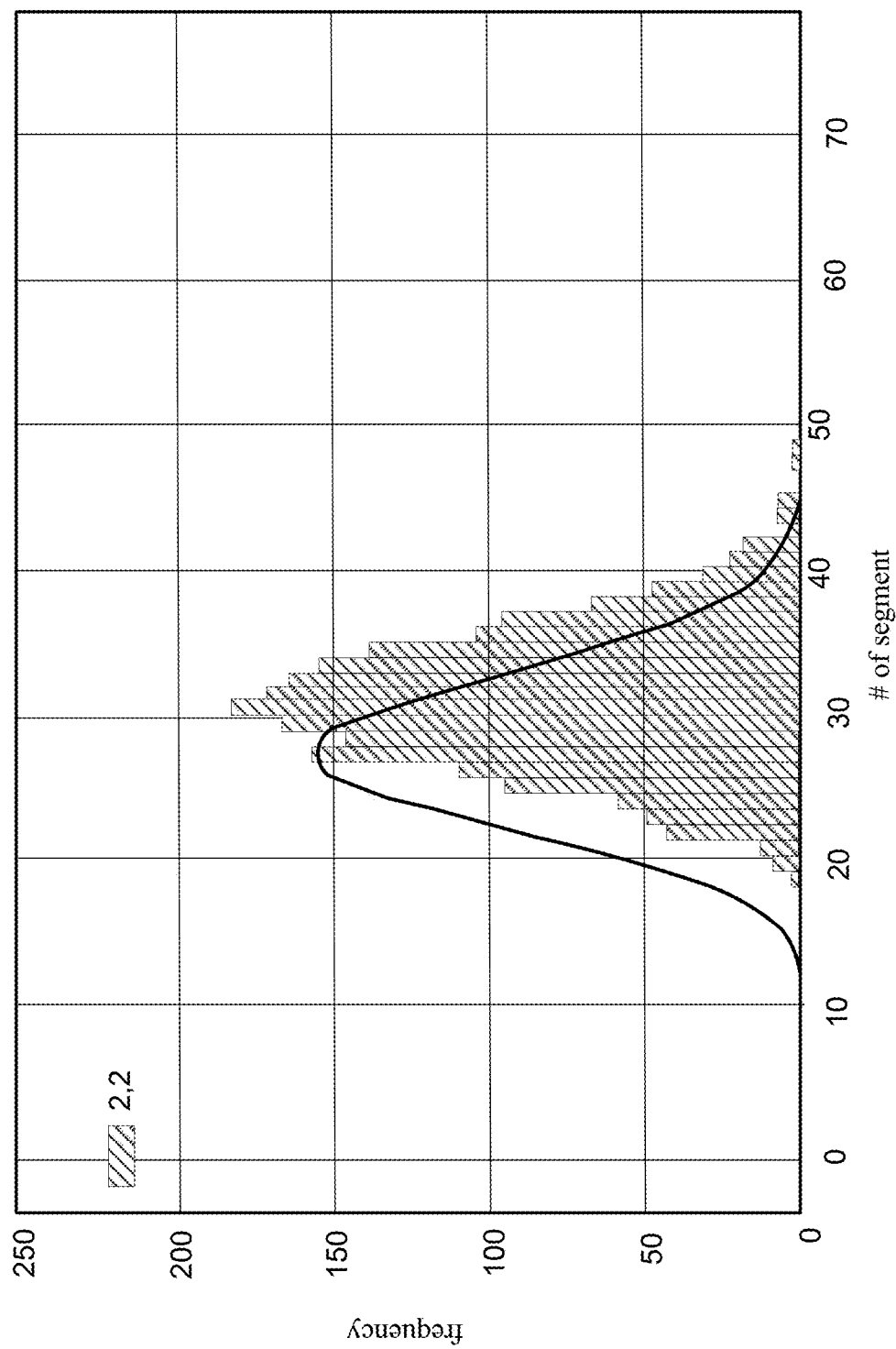
Figure 9C:
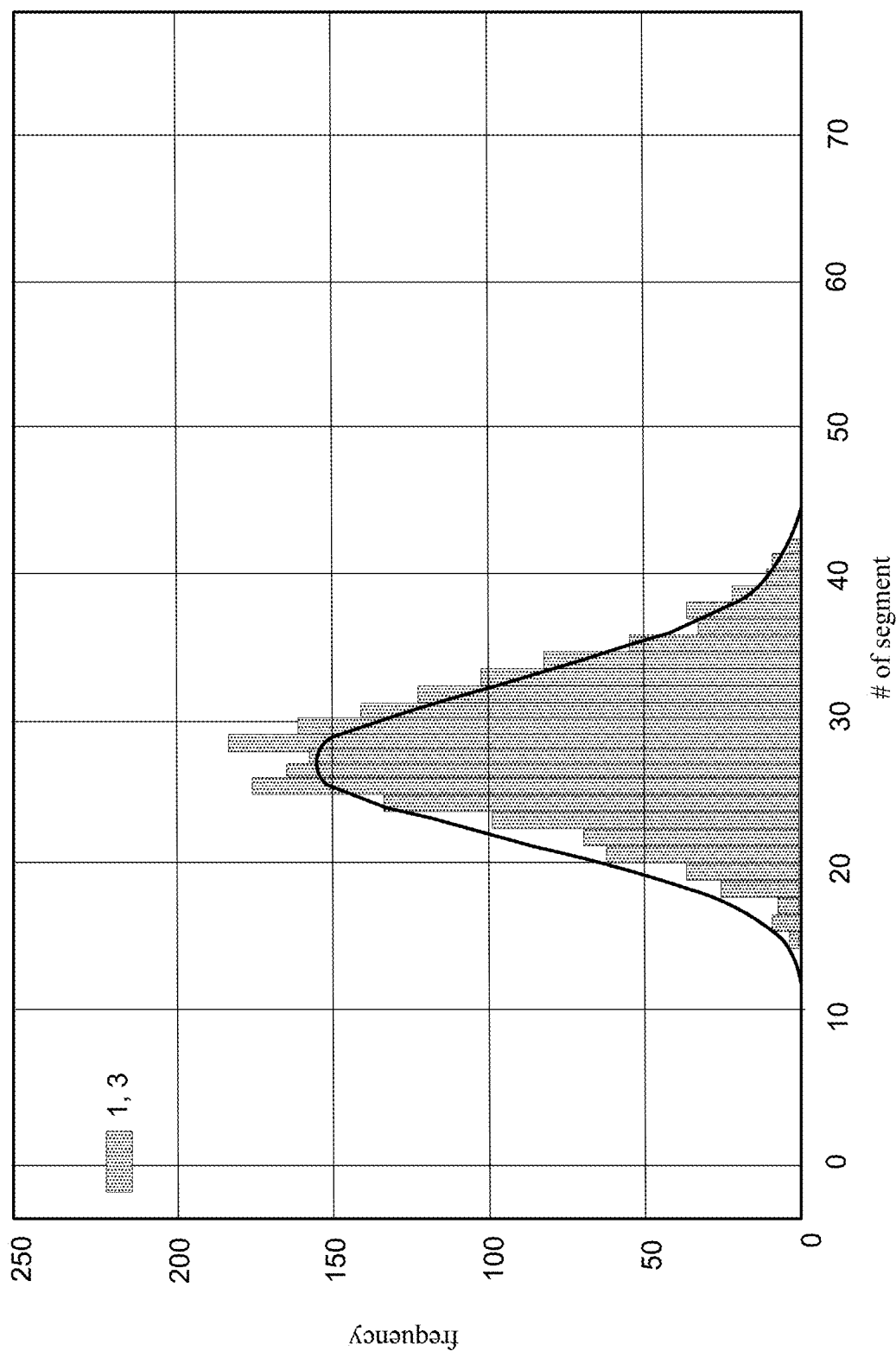

The number of IBD segments (thresholded by u) is modeled as a Poisson random variable with rate parameter λ, with $$\lambda = \frac{\gamma}{100} 2^{-g+1+\delta(i,j)} g e^{-\frac{u}{100}g},$$

where γ is genome length in cM. FIGS. 9A-C illustrates a fit of the simulated match data to this model. FIG. 9A illustrates empirical distribution of segment counts for great grandparent (i.e. g=(0, 3)), FIG. 9B illustrates empirical distribution of segment counts for 1st cousins (i.e. g=(2, 2)), and FIG. 9C illustrates empirical distribution of segment counts for grand aunt/uncle (i.e. g=(1, 3)). The model fit for each model is illustrated in each figure as a solid line.

If no recent common ancestor information is known, the approach is to integrate over all possible generations at which the two individuals could share a CA, and the probability of waiting t generations to find a common ancestor is modeled as a geometric distribution with success rate $$\frac{1}{N_e}$$

where $N_e$ is the effective population size. The segment length distribution is modeled as $$p_{bkgd}(l) = \frac{2N_e(50 + N_e \times \mu)^2}{(50 + l \times N_e)^3}.$$

The number of IBD segments as a Poisson random variable with rate parameter $$\lambda_{bkgd} = \frac{\gamma \times 50 \times N_e}{(50 + N_e \times \mu)^2}.$$

To compute the composite likelihood for a pedigree based on observed IBD segments, consider the individuals in a pedigree of with genetic data and assume the number of such individuals is M. Each pair of individuals i and j in the pedigree has $g_i$ and $g_j$ number of generations to the most recent common ancestor (CA). For ease of notation, g=($g_i$, $g_j$). Let $l^{(ij)}$ denote the observed spectrum of IBD segments between the pair of individuals i and j. For the case when there is no IBD sharing, denote $l^{(ij)}=\{\emptyset\}$. Let the number of segments $n_{ij}=|l_{(ij)}|$. The composite likelihood of g:=$(g_{ij})_{i \neq j}$ is given by:

$$CL(g) = \prod_{i \neq j} P(l^{(ij)} \mid g_{ij})^{\frac{1}{M-1}} = \prod_{i \neq j} \left[ P(N = n_{ij} \mid g_{ij}) \prod_{k=1}^{n_{ij}} q(l_k^{(ij)} \mid g_{ij}) \right]^{\frac{1}{M-1}}$$

Intuitively, the equation above determines a likelihood for each pair of individuals i and j in the pedigree and generates a composite likelihood by multiplying the likelihood for each pair of individuals. The likelihood for each pair of individuals indicates a probability that individuals i and j have $g_i$ and $g_j$ generations away from the common ancestor respectively based on observed IBD segments (i.e. matched DNA data bits). The composite likelihood is determined based on a product of the likelihood for each pair of individuals in the candidate data tree.

Therefore, based on a composite likelihood for each candidate pedigree, it is possible to detect if an individual belongs to a pedigree and where the individual may be positioned in the pedigree based on genetic information. For each operation illustrated in steps 506-510 in FIG. 5, candidate trees may be generated, and a composite likelihood may be calculated for each candidate tree. As such, based on the composite likelihood, the computing server 130 may select a candidate tree with a top-ranking composite likelihood.

Example Application on Simulated Data

Figure 10A:
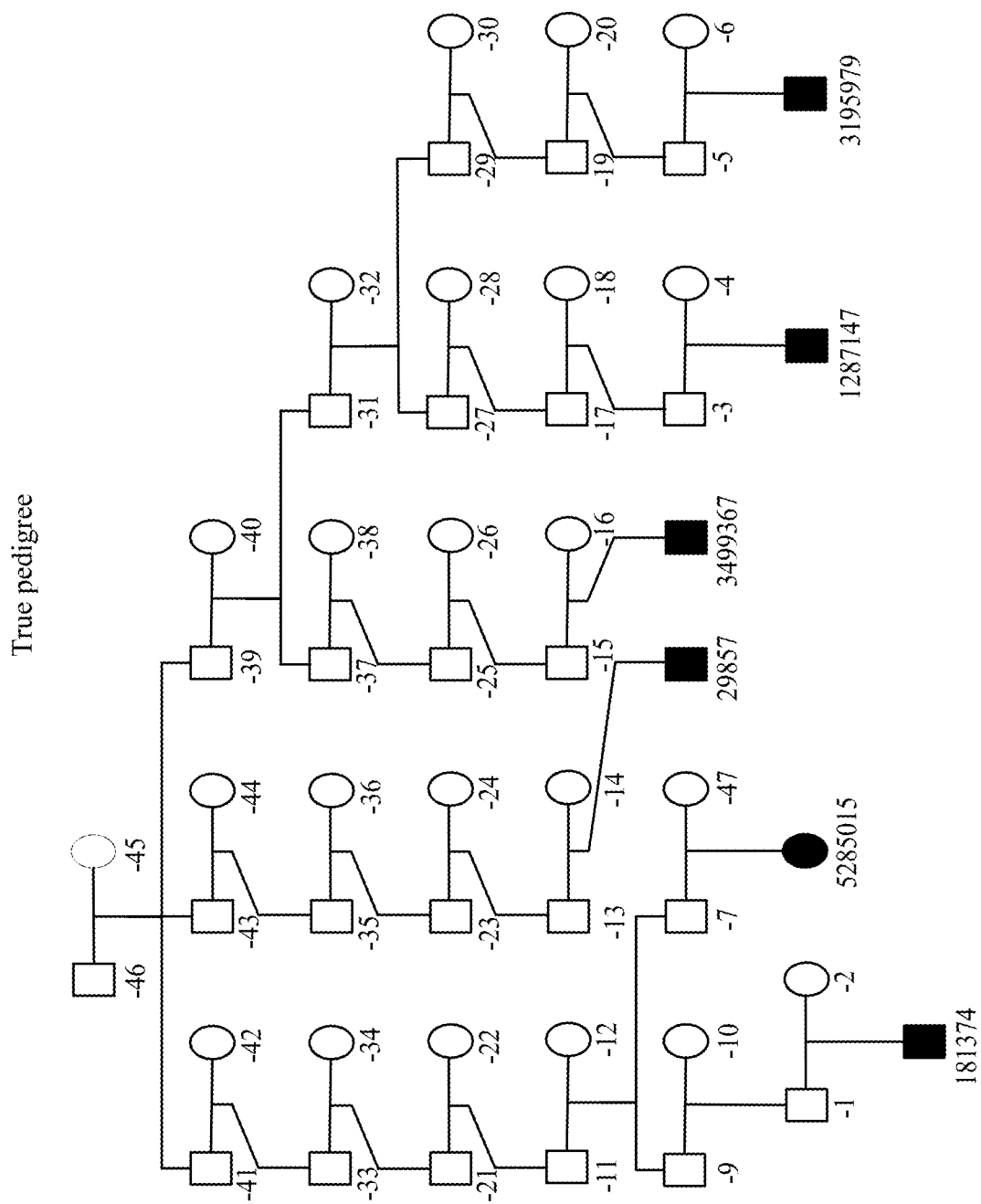
FIG. 10A-B illustrate true pedigree and pedigrees identified by the disclosed method.
Figure 10B:
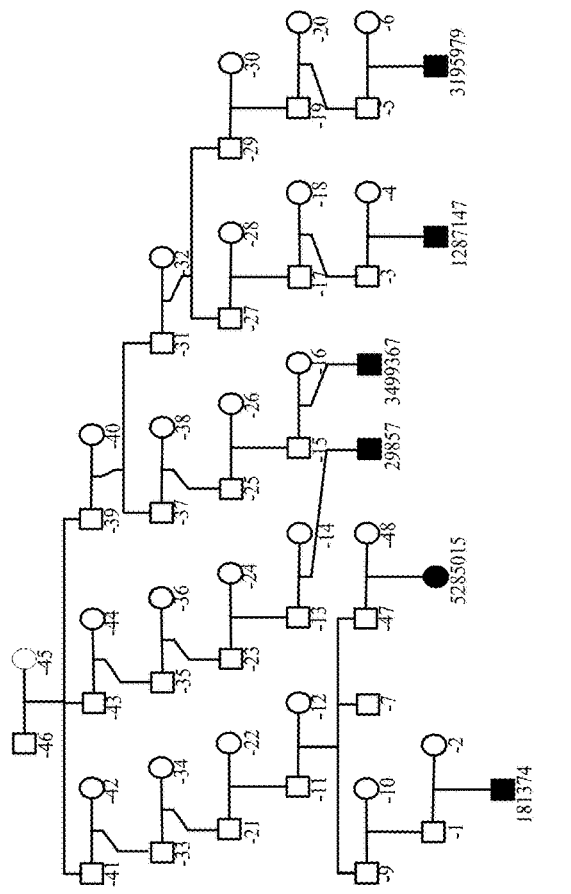
Figure 10B:
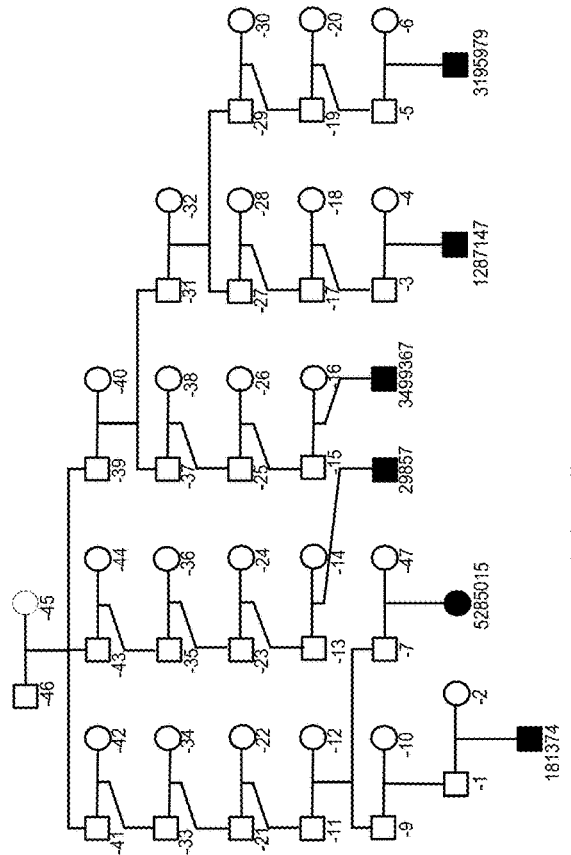

To illustrate with a dataset, a simulated dataset with ground truth is used to compare true pedigree and estimated pedigree with a top-ranking composite likelihood score. First, a group of pedigrees with different sizes and topology are sampled from the large-scale database "big tree" and genetic information for each pedigree is simulated. Information with regard to which individuals have genetic information is included in the pedigree. Then, sample one individual in the pedigree that has genetic information as the target individual and mask the individual off in the individual's respective pedigree. A simulation run is conducted with the ideal outcome to be matching the target individual back to the pedigree that the individual originally belongs to. FIG. 10A illustrates one example of the true pedigree that a target individual belongs to and FIG. 10B illustrates the two pedigrees with top log likelihood identified by the method.

Figure 11:
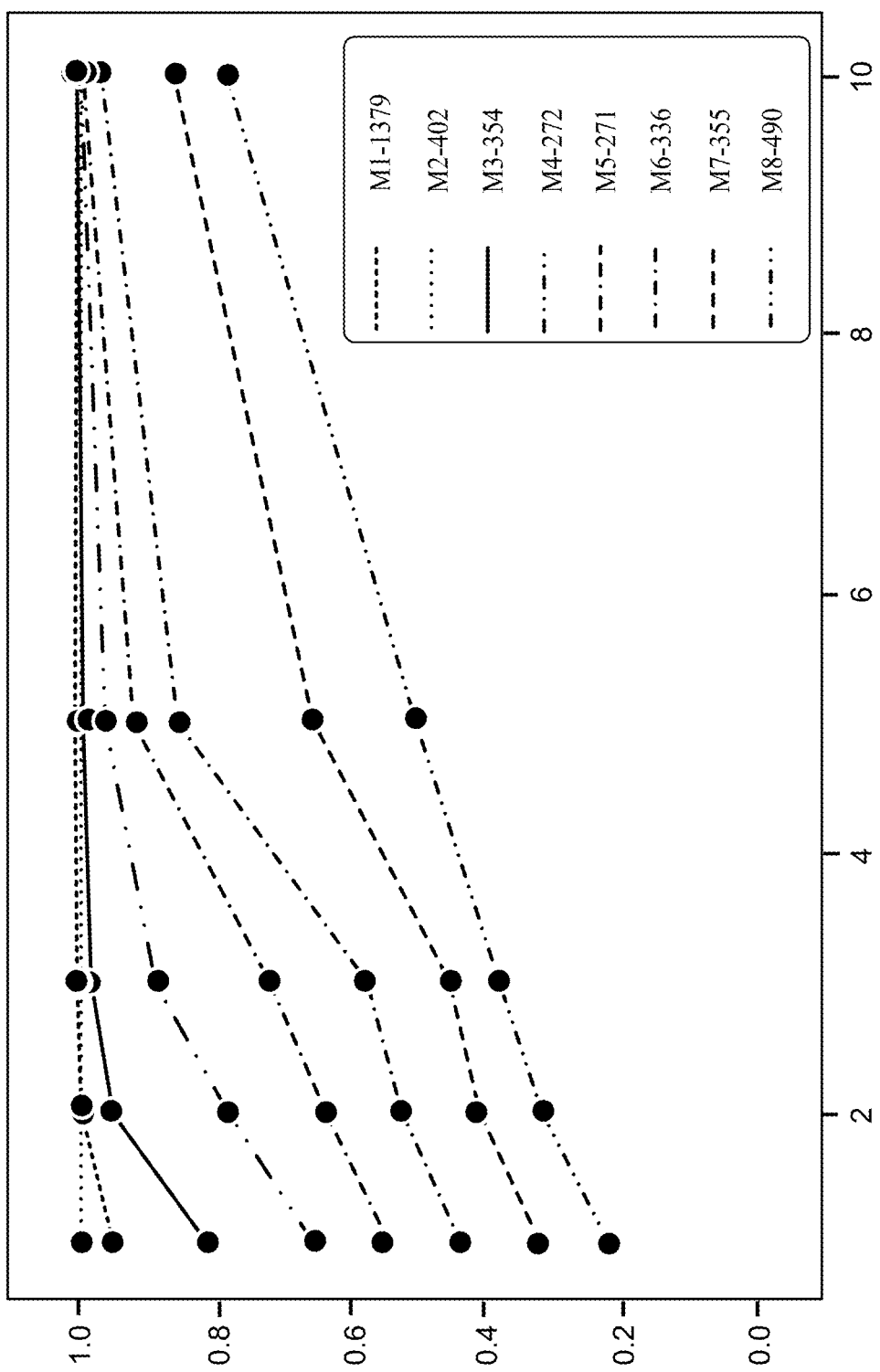
FIG. 11 is a graph that illustrates model performance based on different meiosis levels.

During the simulation, the test pedigrees are grouped into eight groups based on the relationship between the target individual and the individual's closest match in the pedigree. Assume Mn is used to denote the relationship where Mn stands for meiosis level. For example, M1 means that the target individual has at least one match in the pedigree that is one generation away. Intuitively, it is easier to estimate a position to place the target individual in the pedigree if the meiosis level is low. FIG. 11 illustrates the performance for each group of test pedigrees. For M2 cases, the prediction accuracy may reach 100% accuracy with the pedigree with the greatest composite likelihood. For M1 cases, the prediction accuracy may reach 100% with the top 2 ranked pedigrees. When false paternity cases are tested with simulated data (i.e. the target person does not belong to any given pedigree), the chances to detect false paternity is 100%. FIG. 11 illustrates the results associated with different relationships where x axis indicates that the respective top x identified pedigrees and y axis indicates the percentage of test cases that have the true pedigree among top x estimated pedigrees.

As such, the disclosed system identifies one or more pedigrees for the target individual and identifies a position in the pedigrees such that relationships between the target individual and individuals in the data tree are also determined. The disclosed system provides a solution to a challenging problem for existing implementation which is identification of pedigree for a target individual who does not have available pedigree information. The disclosed system is able to identify the most likely potential pedigrees with desirable results for a target individual based on genetic information and available information in the database. Furthermore, the disclosed system improves efficiency because of optimization steps such as pruning, ranking and filtering based on meiosis and generation value information. These steps further filter information that is likely to be not useful and therefore reduces computational complexity.

Calculating M

The evaluation of evidence depends on how m, the tree relationship, is calculated. For a simple case, which is a full relationship with only one pair of observed common ancestors, m is the number of hops between the two individuals (e.g., 1st cousins are m4).

More complicated relationships can be fit into the framework below. (1) For any half relationship between two individuals, use the m(x+1) distribution. (2) Inbreeding adds another path to the common ancestor couple. This acts the same as if there was a completely different ancestor. For example, m8wm6 mg (m8 relationship with an m6 marriage in one of the lines) is the same as m8+m8. If the cousin marriage happens on a path that is longer than the closest path, then that is reflected accordingly (i.e. m8+m9). (3) 2m(x) is equal to m(x−1). That is, m8+m8=m7. (4) m(x)+m(x+1) is equal to a distribution halfway between the m(x) and m(x−1) distributions. In this case, the higher score between the distributions should be used. (5) m(x)+m(x+y) where y>1 is very close to the m(x) distribution. This distribution or the max between the m(x) and m(x−1) distributions could be used.

For example, consider the following relationship:

m7+m8+m8wm7 mg+m9+m9wm6 mg+m10+m10+m11

The above relationship can be simplified by first expanding the marriage inbreeding relationships:

m7+m8+m8+m9+m9+m9+m9+m10+m10+m11

The relationship can be further simplified by considering the combinations of relationships, highest relationships first:

m7+m8+m8+m9+m9+m9+m9+m9+m11 m7+m8+m8+m8+m9+m9+m9+m11 m7+m8+m8+m8+m8+m9+m11 m7+m7+m8+m8+m9+m11 m7+m7+m7+m9+m11 m6+m7+m9+m11

The relationship distribution is expected to be between the m6 and m7 distributions. The computing server 130 may run both m6 and m7 and take the maximum score.

Computing Machine Architecture

Figure 12:
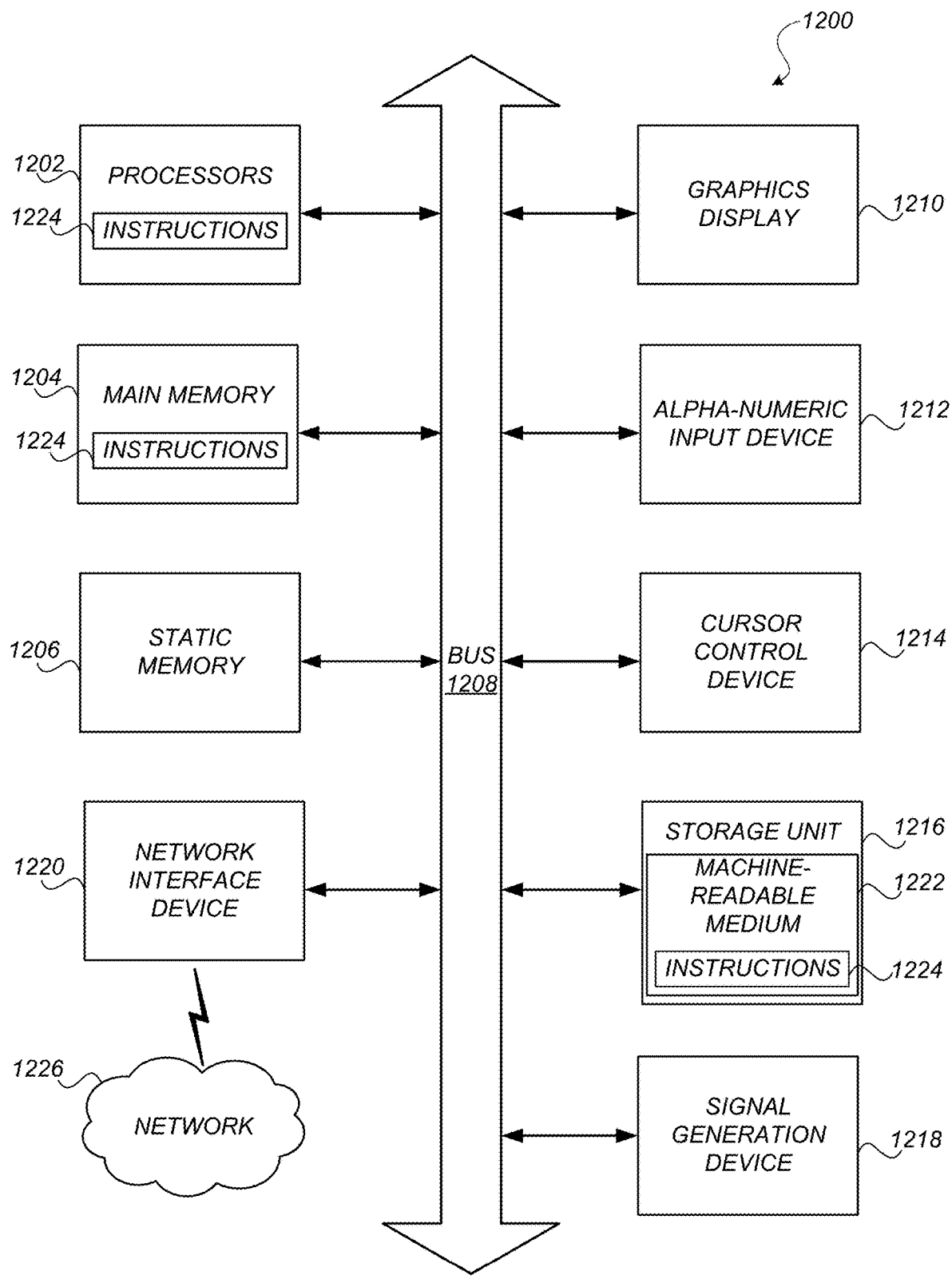
FIG. 12 is a block diagram illustrating an example computer architecture, in accordance with one embodiment.

FIG. 12 is a block diagram illustrating components of an example computing machine that is capable of reading instructions from a computer-readable medium and execute them in a processor (or controller). A computer described herein may include a single computing machine shown in FIG. 12, a virtual machine, a distributed computing system that includes multiples nodes of computing machines shown in FIG. 12, or any other suitable arrangement of computing devices.

By way of example, FIG. 12 shows a diagrammatic representation of a computing machine in the example form of a computer system 1200 within which instructions 1224 (e.g., software, source code, program code, expanded code, object code, assembly code, or machine code), which may be stored in a computer-readable medium for causing the machine to perform any one or more of the processes discussed herein may be executed. In some embodiments, the computing machine operates as a standalone device or may be connected (e.g., networked) to other machines. In a networked deployment, the machine may operate in the capacity of a server machine or a client machine in a server-client network environment, or as a peer machine in a peer-to-peer (or distributed) network environment.

The structure of a computing machine described in FIG. 12 may correspond to any software, hardware, or combined components shown in FIGS. 1 and 2, including but not limited to, the client device 110, the computing server 130, and various engines, interfaces, terminals, and machines shown in FIG. 2. While FIG. 12 shows various hardware and software elements, each of the components described in FIGS. 1 and 2 may include additional or fewer elements.

By way of example, a computing machine may be a personal computer (PC), a tablet PC, a set-top box (STB), a personal digital assistant (PDA), a cellular telephone, a smartphone, a web appliance, a network router, an internet of things (IoT) device, a switch or bridge, or any machine capable of executing instructions 1224 that specify actions to be taken by that machine. Further, while only a single machine is illustrated, the term "machine" and "computer" may also be taken to include any collection of machines that individually or jointly execute instructions 1224 to perform any one or more of the methodologies discussed herein.

The example computer system 1200 includes one or more processors 1202 such as a CPU (central processing unit), a GPU (graphics processing unit), a TPU (tensor processing unit), a DSP (digital signal processor), a system on a chip (SOC), a controller, a state equipment, an application-specific integrated circuit (ASIC), a field-programmable gate array (FPGA), or any combination of these. Parts of the computing system 1200 may also include a memory 1204 that store computer code including instructions 1224 that may cause the processors 1202 to perform certain actions when the instructions are executed, directly or indirectly by the processors 1202. Instructions can be any directions, commands, or orders that may be stored in different forms, such as equipment-readable instructions, programming instructions including source code, and other communication signals and orders. Instructions may be used in a general sense and are not limited to machine-readable codes. One or more steps in various processes described may be performed by passing through instructions to one or more multiply-accumulate (MAC) units of the processors.

One and more methods described herein improve the operation speed of the processors 1202 and reduces the space required for the memory 1204. For example, the database processing techniques and machine learning methods described herein reduce the complexity of the computation of the processors 1202 by applying one or more novel techniques that simplify the steps in training, reaching convergence, and generating results of the processors 1202. The algorithms described herein also reduces the size of the models and datasets to reduce the storage space requirement for memory 1204.

The performance of certain of the operations may be distributed among the more than processors, not only residing within a single machine, but deployed across a number of machines. In some example embodiments, the one or more processors or processor-implemented modules may be located in a single geographic location (e.g., within a home environment, an office environment, or a server farm). In other example embodiments, the one or more processors or processor-implemented modules may be distributed across a number of geographic locations. Even though in the specification or the claims may refer some processes to be performed by a processor, this should be construed to include a joint operation of multiple distributed processors.

The computer system 1200 may include a main memory 1204, and a static memory 1206, which are configured to communicate with each other via a bus 1208. The computer system 1200 may further include a graphics display unit 1210 (e.g., a plasma display panel (PDP), a liquid crystal display (LCD), a projector, or a cathode ray tube (CRT)). The graphics display unit 1210, controlled by the processors 1202, displays a graphical user interface (GUI) to display one or more results and data generated by the processes described herein. The computer system 1200 may also include alphanumeric input device 1212 (e.g., a keyboard), a cursor control device 1214 (e.g., a mouse, a trackball, a joystick, a motion sensor, or other pointing instrument), a storage unit 1216 (a hard drive, a solid state drive, a hybrid drive, a memory disk, etc.), a signal generation device 1218 (e.g., a speaker), and a network interface device 1220, which also are configured to communicate via the bus 1208.

The storage unit 1216 includes a computer-readable medium 1222 on which is stored instructions 1224 embodying any one or more of the methodologies or functions described herein. The instructions 1224 may also reside, completely or at least partially, within the main memory 1204 or within the processor 1202 (e.g., within a processor's cache memory) during execution thereof by the computer system 1200, the main memory 1204 and the processor 1202 also constituting computer-readable media. The instructions 1224 may be transmitted or received over a network 1226 via the network interface device 1220.

While computer-readable medium 1222 is shown in an example embodiment to be a single medium, the term "computer-readable medium" should be taken to include a single medium or multiple media (e.g., a centralized or distributed database, or associated caches and servers) able to store instructions (e.g., instructions 1224). The computer-readable medium may include any medium that is capable of storing instructions (e.g., instructions 1224) for execution by the processors (e.g., processors 1202) and that cause the processors to perform any one or more of the methodologies disclosed herein. The computer-readable medium may include, but not be limited to, data repositories in the form of solid-state memories, optical media, and magnetic media. The computer-readable medium does not include a transitory medium such as a propagating signal or a carrier wave.

ADDITIONAL CONSIDERATIONS

The foregoing description of the embodiments has been presented for the purpose of illustration; it is not intended to be exhaustive or to limit the patent rights to the precise forms disclosed. Persons skilled in the relevant art can appreciate that many modifications and variations are possible in light of the above disclosure.

Any feature mentioned in one claim category, e.g. method, can be claimed in another claim category, e.g. computer program product, system, storage medium, as well. The dependencies or references back in the attached claims are chosen for formal reasons only. However, any subject matter resulting from a deliberate reference back to any previous claims (in particular multiple dependencies) can be claimed as well, so that any combination of claims and the features thereof is disclosed and can be claimed regardless of the dependencies chosen in the attached claims. The subject-matter may include not only the combinations of features as set out in the disclosed embodiments but also any other combination of features from different embodiments. Various features mentioned in the different embodiments can be combined with explicit mentioning of such combination or arrangement in an example embodiment or without any explicit mentioning. Furthermore, any of the embodiments and features described or depicted herein may be claimed in a separate claim and/or in any combination with any embodiment or feature described or depicted herein or with any of the features.

Some portions of this description describe the embodiments in terms of algorithms and symbolic representations of operations on information. These operations and algorithmic descriptions, while described functionally, computationally, or logically, are understood to be implemented by computer programs or equivalent electrical circuits, microcode, or the like. Furthermore, it has also proven convenient at times, to refer to these arrangements of operations as engines, without loss of generality. The described operations and their associated engines may be embodied in software, firmware, hardware, or any combinations thereof.

Any of the steps, operations, or processes described herein may be performed or implemented with one or more hardware or software engines, alone or in combination with other devices. In one embodiment, a software engine is implemented with a computer program product comprising a computer-readable medium containing computer program code, which can be executed by a computer processor for performing any or all of the steps, operations, or processes described. The term "steps" does not mandate or imply a particular order. For example, while this disclosure may describe a process that includes multiple steps sequentially with arrows present in a flowchart, the steps in the process do not need to be performed by the specific order claimed or described in the disclosure. Some steps may be performed before others even though the other steps are claimed or described first in this disclosure. Likewise, any use of (i), (ii), (iii), etc., or (a), (b), (c), etc. in the specification or in the claims, unless specified, is used to better enumerate items or steps and also does not mandate a particular order.

Throughout this specification, plural instances may implement components, operations, or structures described as a single instance. Although individual operations of one or more methods are illustrated and described as separate operations, one or more of the individual operations may be performed concurrently, and nothing requires that the operations be performed in the order illustrated. Structures and functionality presented as separate components in example configurations may be implemented as a combined structure or component. Similarly, structures and functionality presented as a single component may be implemented as separate components. These and other variations, modifications, additions, and improvements fall within the scope of the subject matter herein. In addition, the term "each" used in the specification and claims does not imply that every or all elements in a group need to fit the description associated with the term "each." For example, "each member is associated with element A" does not imply that all members are associated with an element A. Instead, the term "each" only implies that a member (of some of the members), in a singular form, is associated with an element A. In claims, the use of a singular form of a noun may imply at least one element even though a plural form is not used.

Finally, the language used in the specification has been principally selected for readability and instructional purposes, and it may not have been selected to delineate or circumscribe the patent rights. It is therefore intended that the scope of the patent rights be limited not by this detailed description, but rather by any claims that issue on an application based hereon. Accordingly, the disclosure of the embodiments is intended to be illustrative, but not limiting, of the scope of the patent rights.

The following applications are incorporated by reference in their entirety for all purposes: (1) U.S. patent application Ser. No. 15/519,099, entitled "Haplotype Phasing Models," filed on Oct. 19, 2015, (2) U.S. patent application Ser. No. 15/168,011, entitled "Discovering Population Structure from Patterns of Identity-By-Descent," filed on May 28, 2016, (3) U.S. patent application Ser. No. 15/519,104 "Reducing Error in Predicted Genetic Relationships," filed on Apr. 13, 2017, (4) U.S. patent application Ser. No. 15/209,458, entitled "Local Genetic Ethnicity Determination System," filed on Jul. 13, 2016, and (5) U.S. patent application Ser. No. 14/029,765, entitled "Identifying Ancestral Relationships Using a Continuous stream of Input," filed on Sep. 17, 2013.

What is claimed is:

1. A computer-implemented method comprising:
receiving a target individual dataset associated with a target individual;
identifying a plurality of candidate individual datasets that are potentially related to the target individual dataset;
identifying a related individual dataset from the plurality of candidate individual datasets, wherein the related individual dataset has data bits that match at least a portion of data bits in the target individual dataset, wherein identifying the related individual dataset comprises:
phasing a genotype corresponding to the target individual and a genotype corresponding to the related individual;
identifying identity by descent (IBD) segments shared between the phased genotype of the target individual dataset and the phased genotype of the related individual dataset;
determining a total length of the IBD segments shared between the phased genotype of the target individual dataset and the phased genotype of the related individual dataset; and
determining that the total length of shared IBD segments exceeds a threshold;
identifying a parent node that is a common parent node for both the related individual dataset and the target individual dataset;
retrieving a data tree to which the parent node belongs, the data tree describing inter-relationships among datasets in the data tree;
identifying, based on strings of matched data bits and number of the strings of matched data bits between the target individual dataset and the datasets in the data tree, a descendant position to the common parent node in the data tree to which the target individual dataset is assigned, wherein identifying the descendant position to the common parent node in the data tree comprises:
generating a plurality of candidate data trees that have the individual dataset assigned to different candidate descendant positions to the common parent node, wherein generating the plurality of candidate data trees comprises:
generating a first candidate data tree that is based on the data tree to which the parent node belongs, the first candidate data tree being the data tree with a first new descendant position, the first candidate data tree adding the individual dataset to the first new descendant position, and
generating a second candidate data tree that is based on the data tree to which the parent node belongs, the second candidate data tree being the data tree with a second new descendant position, the second candidate data tree adding the individual dataset to the second new descendant position,
calculating, for each of the candidate data trees with new descendant positions added for the individual dataset to the common parent node, a plurality of pairwise relationship likelihoods, each pairwise relationship likelihood measuring a likelihood between a candidate descendant position and another dataset that also represents a descendant of the common parent node, and
selecting a candidate data tree as the data tree based on the plurality of pairwise relationship likelihoods; and
outputting the data tree with the target individual dataset located in the descendant position.

2. The method of claim 1, wherein identifying a parent node further comprises:
identifying a plurality of candidate parent nodes, wherein a candidate parent node represents a candidate common ancestor for both the target individual dataset and one of the candidate individual datasets;
calculating confidence scores for the candidate parent nodes; and
selecting one of the candidate parent nodes as the parent node based on a ranking of the candidate parent nodes by the confidence scores.

3. The method of claim 2, wherein identifying the parent node further comprises a pruning process, the pruning process comprising:
retrieving a meiosis separation between the related individual represented by the related individual dataset and the target individual;
determining a generation value between the related individual and one of the candidate parent nodes;
determining a range for the generation value based on the meiosis; and
removing the one of the candidate parent nodes as a candidate in response to the generation value out of the range.

4. The method of claim 1, wherein generating the plurality of candidate data trees that have the individual dataset assigned to different candidate descendant positions to the common parent node comprises one or more of the following:
(i) assigning the target individual dataset at an existing node in the data tree as the one of the new descendant positions, the one of the new descendant positions replacing the existing node;

(ii) adding a child node that descends from a leaf node in the data tree as the one of the new descendant positions of the target individual dataset; and/or (iii) adding a child node that descends from an inner node in the data tree wherein the child node is in a new branch descending from the inner node, the child node being the one of the new descendant positions of the target individual dataset.

5. The method of claim 1, wherein each candidate data is associated with a likelihood score determined from the pairwise relationship likelihoods, the likelihood score for each candidate data tree is a composite likelihood calculated based on individual datasets in each candidate data tree, wherein the individual datasets contain DNA information.

6. The method of claim 5, wherein the composite likelihood for each candidate data tree is determined based on steps comprising:
determining a likelihood for each pairwise individual datasets between the target individual and other individuals in the candidate data tree, the pairwise individual datasets containing DNA information in the candidate data tree, the likelihood calculated based on matched DNA information and positions of the pair of individual datasets in the candidate data tree; and
generating the composite likelihood based on a product of the likelihood of each pair of individual datasets.

7. The method of claim 1, wherein identifying the descendant position to the common parent node in the data tree to which the target individual dataset is assigned is further based on a relationship between the target individual dataset and the related individual dataset determined based on matched DNA information.

8. The method of claim 1, wherein:
the data bits contain information associated with DNA;
the strings of matched data bits contain information associated with matched DNA segments; and
the number of the strings contain information associated with number of matched DNA segments.

9. The computer-implemented method of claim 1, wherein identifying a parent node that is a common parent node for both the related individual dataset and the target individual dataset comprises:
identifying a data tree corresponding to the target individual dataset and a data tree corresponding to the related individual dataset in a large-scale network comprising concatenated data trees corresponding to a plurality of individuals, the concatenated data trees having been linked in the large-scale network by identifying common individuals in different data trees, and
identifying a parent node by defining a path connecting the target individual dataset and the related individual dataset in the large-scale network.

10. A system comprising:
a computing server comprising one or more processors and memory for storing computer code comprising instructions, wherein the instructions, when executed by one or more computer processors, cause the one or more computer processors to perform steps comprising:
receiving a target individual dataset associated with a target individual;
identifying a plurality of candidate individual datasets that are potentially related to the target individual dataset;
identifying a related individual dataset from the plurality of candidate individual datasets, wherein the related individual dataset has data bits that match at least a portion of data bits in the target individual dataset, wherein identifying the related individual dataset comprises:
phasing a genotype corresponding to the target individual and a genotype corresponding to the related individual;
identifying identity by descent (IBD) segments shared between the phased genotype of the target individual dataset and the phased genotype of the related individual dataset;
determining a total length of the IBD segments shared between the phased genotype of the target individual dataset and the phased genotype of the related individual dataset; and
determining that the total length of shared IBD segments exceeds a threshold;
identifying a parent node that is a common parent node for both the related individual dataset and the target individual dataset;
retrieving a data tree to which the parent node belongs, the data tree describing inter-relationships among datasets in the data tree;
identifying, based on strings of matched data bits and number of the strings of matched data bits between the target individual dataset and the datasets in the data tree, a descendant position to the common parent node in the data tree to which the target individual dataset is assigned, wherein identifying the descendant position to the common parent node in the data tree comprises:
generating a plurality of candidate data trees that have the individual dataset assigned to different candidate descendant positions to the common parent node, wherein generating the plurality of candidate data trees comprises:
generating a first candidate data tree that is based on the data tree to which the parent node belongs, the first candidate data tree being the data tree with a first new descendant position, the first candidate data tree adding the individual dataset to the first new descendant position, and generating a second candidate data tree that is based on the data tree to which the parent node belongs, the second candidate data tree being the data tree with a second new descendant position, the second candidate data tree adding the individual dataset to the second new descendant position,
calculating, for each of the candidate data trees with new descendant positions added for the individual dataset to the common parent node, a plurality of pairwise relationship likelihoods, each pairwise relationship likelihood measuring a likelihood between a candidate descendant position and another dataset that also represents a descendant of the common parent node, and
selecting a candidate data tree as the data tree based on the plurality of pairwise relationship likelihoods; and
outputting the data tree with the target individual dataset located in the descendant position; and
a graphical user interface in communication with the computing server, the graphical user interface configured to display the data tree with the target individual dataset located in the descendant position.

11. The system of claim 10, wherein identifying a parent node further comprises:
identifying a plurality of candidate parent nodes, wherein a candidate parent node represents a candidate common ancestor for both the target individual dataset and one of the candidate individual datasets;
calculating confidence scores for the candidate parent nodes; and selecting one of the candidate parent nodes as the parent node based on a ranking of the candidate parent nodes by the confidence scores.

12. The system of claim 11, wherein identifying the parent node further comprises a pruning process, the pruning process comprising:
retrieving a meiosis separation between the related individual represented by the related individual dataset and the target individual;
determining a generation value between the related individual and one of the candidate parent nodes;
determining a range for the generation value based on the meiosis; and
removing the one of the candidate parent nodes as a candidate in response to the generation value out of the range.

13. The system of claim 10, wherein generating one or more candidate data trees that have the individual dataset assigned to different candidate descendant positions to the common parent node comprises one or more of the following:
(i) assigning the target individual dataset at an existing node in the data tree as the one of the new descendant positions, the new descendant positions replacing the existing node;
(ii) adding a child node that descends from a leaf node in the data tree as the one of the new descendant positions of the target individual dataset; and/or
(iii) adding a child node that descends from an inner node in the data tree wherein the child node is in a new branch descending from the inner node, the child node being the one of the new descendant positions of the target individual dataset.

14. The system of claim 10, wherein each candidate data is associated with a likelihood score determined from the pairwise relationship likelihoods, the likelihood score for each candidate data tree is a composite likelihood calculated based on individual datasets in each candidate data tree, wherein the individual datasets contain DNA information.

15. The system of claim 14, wherein the composite likelihood for each candidate data tree is determined based on steps comprising:
determining a likelihood for each pairwise individual datasets between the target individual and other individuals in the candidate data tree, the pairwise individual datasets containing DNA information in the candidate data tree, the likelihood calculated based on matched DNA information and positions of the pair of individual datasets in the candidate data tree; and
generating the composite likelihood based on a product of the likelihood of each pair of individual datasets.

16. The system of claim 10, wherein identifying the descendant position to the common parent node in the data tree to which the target individual dataset is assigned is further based on metadata associated with the datasets.

17. The system of claim 10, wherein identifying the descendant position to the common parent node in the data tree to which the target individual dataset is assigned is further based on a relationship between the target individual dataset and the related individual dataset determined based on matched DNA information.

18. A non-transitory computer readable medium for storing computer code comprising instructions for linking an individual dataset to a database, the instructions, when executed by one or more computer processors, cause the one or more computer processors to perform steps comprising:
receiving a target individual dataset associated with a target individual;
identifying a plurality of candidate individual datasets that are potentially related to the target individual dataset;
identifying a related individual dataset from the plurality of candidate individual datasets, wherein the related individual dataset has data bits that match at least a portion of data bits in the target individual dataset, wherein identifying the related individual dataset comprises:
phasing a genotype corresponding to the target individual and a genotype corresponding to the related individual;
identifying identity by descent (IBD) segments shared between the phased genotype of the target individual dataset and the phased genotype of the related individual dataset;
determining a total length of the IBD segments shared between the phased genotype of the target individual dataset and the phased genotype of the related individual dataset; and
determining that the total length of shared IBD segments exceeds a threshold;
identifying a parent node that is a common parent node for both the related individual dataset and the target individual dataset;
retrieving a data tree to which the parent node belongs, the data tree describing inter-relationships among datasets in the data tree;
identifying, based on strings of matched data bits and number of the strings of matched data bits between the target individual dataset and the datasets in the data tree, a descendant position to the common parent node in the data tree to which the target individual dataset is assigned, wherein identifying the descendant position to the common parent node in the data tree comprises:
generating a plurality of candidate data trees that have the individual dataset assigned to different candidate descendant positions to the common parent node, wherein generating the plurality of candidate data trees comprises:
generating a first candidate data tree that is based on the data tree to which the parent node belongs, the first candidate data tree being the data tree with a first new descendant position, the first candidate data tree adding the individual dataset to the first new descendant position, and
generating a second candidate data tree that is based on the data tree to which the parent node belongs, the second candidate data tree being the data tree with a second new descendant position, the second candidate data tree adding the individual dataset to the second new descendant position,
calculating, for each of the candidate data trees with new descendant positions added for the individual dataset to the common parent node, a plurality of pairwise relationship likelihoods, each pairwise relationship likelihood measuring a likelihood between a candidate descendant position and another dataset that also represents a descendant of the common parent node, and
selecting a candidate data tree as the data tree based on the plurality of pairwise relationship likelihoods; and
outputting the data tree with the target individual dataset located in the descendant position.

* * * * *